US011312994B2

(12) United States Patent
Soykan et al.

(10) Patent No.: US 11,312,994 B2
(45) Date of Patent: Apr. 26, 2022

(54) METHODS AND COMPOSITIONS FOR SCD, CRT, CRT-D, OR SCA THERAPY IDENTIFICATION AND/OR SELECTION

(71) Applicant: Medtronic, Inc., Minneapolis, MN (US)

(72) Inventors: Orhan Soykan, Shoreview, MN (US); Tara Nahey, Minneapolis, MN (US); Jeffrey Lande, Minneapolis, MN (US)

(73) Assignee: Medtronic, Inc, Minneapolis, MN (US)

( * ) Notice: Subject to any disclaimer, the term of this patent is extended or adjusted under 35 U.S.C. 154(b) by 261 days.

(21) Appl. No.: 16/149,560

(22) Filed: Oct. 2, 2018

(65) Prior Publication Data

US 2019/0017120 A1 Jan. 17, 2019

Related U.S. Application Data

(62) Division of application No. 14/698,812, filed on Apr. 28, 2015, now abandoned.

(60) Provisional application No. 62/104,098, filed on Jan. 16, 2015, provisional application No. 61/988,323, filed on May 5, 2014.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 5,433,946 | A | 7/1995 | Allen |
| 5,474,796 | A | 12/1995 | Brennan |
| 5,814,014 | A | 9/1998 | Elsberry |
| 6,015,572 | A | 1/2000 | Lin |
| 6,056,725 | A | 5/2000 | Elsberry |
| 6,099,469 | A | 8/2000 | Armstrong |
| 6,368,823 | B1 | 4/2002 | Bril |
| 6,436,392 | B1 | 8/2002 | Engelhardt |
| 6,436,708 | B1 | 8/2002 | Leone |
| 6,468,524 | B1 | 10/2002 | Chiorini |
| 6,500,630 | B2 | 12/2002 | Conover |
| 6,597,952 | B1 | 7/2003 | Mika |
| 7,048,716 | B1 | 5/2006 | Kucharczyk |
| 7,361,468 | B2 | 4/2008 | Liu |
| 2001/0053519 | A1 | 12/2001 | Fodor |
| 2002/0076394 | A1 | 6/2002 | Leone |
| 2002/0165161 | A1 | 11/2002 | Allison |
| 2003/0092019 | A1 | 5/2003 | Meyer |
| 2003/0129186 | A1 | 7/2003 | Beliveau |
| 2003/0019063 | A1 | 10/2003 | McSwiggen |
| 2004/0162255 | A1 | 8/2004 | Kaemmerer |
| 2005/0032733 | A1 | 2/2005 | McSwiggen |
| 2005/0177196 | A1 | 8/2005 | Soykan |
| 2005/0181386 | A1 | 8/2005 | Diamond |
| 2005/0191731 | A1 | 9/2005 | Judson |
| 2005/0266576 | A1 | 12/2005 | Soykan |
| 2005/0287574 | A1 | 12/2005 | Soykan et al. |
| 2006/0013456 | A1 | 1/2006 | Soykan |
| 2006/0018882 | A1 | 1/2006 | Kaemmerer |
| 2006/0019397 | A1 | 1/2006 | Soykan |
| 2006/0024715 | A1 | 2/2006 | Liu |
| 2006/0147936 | A1 | 7/2006 | Frey |
| 2007/0038386 | A1 | 2/2007 | Schadt |
| 2007/0042382 | A1 | 2/2007 | Cargill et al. |
| 2007/0054278 | A1 | 3/2007 | Cargill |
| 2007/0082347 | A1 | 4/2007 | Lanchbury |
| 2008/0020385 | A1 | 1/2008 | Frey |
| 2009/0131276 | A1 | 5/2009 | Soykan |
| 2009/0136954 | A1 | 5/2009 | Soykan |
| 2009/0220954 | A1 | 9/2009 | Doria et al. |
| 2010/0047915 | A1 | 2/2010 | Soykan |
| 2010/0317006 | A1 | 12/2010 | Soykan |
| 2011/0143345 | A1 | 6/2011 | Soykan et al. |
| 2011/0143956 | A1 | 6/2011 | Soykan |

(Continued)

FOREIGN PATENT DOCUMENTS

| DE | 10348600 | 9/2004 |
| EP | 0002404 | 6/1979 |

(Continued)

OTHER PUBLICATIONS

Database EMBL, PM1008J11TR BAC library from the prostate metastasis sample 25 *Homo sapiens* genomic clone PM1_J11, genomic survey sequence, XP0000026569685, retrieved from EBI accession No. EM-GSS:E1774795, dated Nov. 1, 2007.
RefSeq SNP report: rs1439098, dated Aug. 3, 2011.
Furakhia et al., Sudden Cardiac death: epidemiology, mechanisms, and therapy, 32:501-546, dated Sep. 1, 2007.
Wieneke et al., Better identification of patients who benefit from implantable cardioverter defibrillators by genotyping the G protein B3 subunit (GNB3) C825T polymorphism, 101: 447-451, dated Jun. 16, 2006.

(Continued)

*Primary Examiner* — Jehanne S Sitton

(57) ABSTRACT

Compositions, polynucleotides, probes, kits, methods, computer systems, treatment methods and genetic markers useful for assessing the risk of Sudden Cardiac Death (SCD), Sudden Cardiac Arrest (SCA), Ventricular Arrhythmia (VA), or Heart Failure (HF) are provided herein. The compositions, polynucleotides, probes, kits, methods, computer systems, treatment methods and genetic markers of the invention can provide patients selection for those that can be treated with an ICD or CRT-D based on assessing the presence of one or more Single Nucleotide Polymorphisms (SNPs) associated with any one of Sudden Cardiac Death (SCD), Sudden Cardiac Arrest (SCA), Ventricular Arrhythmia (VA), or Heart Failure (HF), and can indicate treatment with certain drugs such as beta-blockers.

15 Claims, 14 Drawing Sheets

Specification includes a Sequence Listing.

(56) References Cited

U.S. PATENT DOCUMENTS

| | | |
|---|---|---|
| 2011/0213328 A1 | 9/2011 | Keimel |
| 2012/0059778 A1 | 3/2012 | Soykan |
| 2012/0309641 A1 | 12/2012 | Soykan |

FOREIGN PATENT DOCUMENTS

| | | |
|---|---|---|
| EP | 0072513 | 3/1989 |
| EP | 0962878 | 8/1999 |
| EP | 1480251 A | 11/2004 |
| WO | WO8201995 | 6/1982 |
| WO | WO1995005864 | 3/1995 |
| WO | WO95111995 | 5/1995 |
| WO | WO9843630 | 10/1998 |
| WO | WO1998046273 | 10/1998 |
| WO | WO2001 070276 | 9/2001 |
| WO | WO02052033 | 7/2002 |
| WO | WO200263959 | 8/2002 |
| WO | WO2002056937 | 10/2002 |
| WO | WO2003044057 | 5/2003 |
| WO | WO3087819 A1 | 10/2003 |
| WO | WO2004047872 | 6/2004 |
| WO | WO2004076690 | 9/2004 |
| WO | WO2006132983 | 12/2006 |
| WO | WO2008054544 | 5/2008 |
| WO | WO2009064970 | 5/2009 |
| WO | WO2012094651 | 7/2012 |

OTHER PUBLICATIONS

International HapMap Project, protocols for HapMap assay-design, dated Oct. 13, 2005.
Stevens, Oxidative-Nitrosative Stress as a contributing factor to cardiovascular disease in subjects with diabetes, 3, 253-266, dated Jan. 1, 2005.
Suzuki et al., Molecular basis of neonatal diabetes in Japanese patients, 92(10):3979-3985, dated Jul. 17, 2007.
RefSNP cluster report: rs564275, dated Mar. 31, 2009.
RefSNP cluster report: rs2716727, dated Mar. 31, 2009.
RefSNP cluster report: rs6974082, dated Mar. 31, 2009.
RefSNP cluster report: rs12666315, dated Mar. 31, 2009.
RefSNP cluster report: rs1439098, dated Mar. 31, 2009.
Xiao et al., Poly (ADP-ribose) polymerase promotes cardiac remodeling, contractile failure, and translocation of apoptosis-inducing factor in a murine experimental model of aortic banding and heart failure, 112, 891-898, dated Jan. 1, 2005.
RefSNP cluster report: rs10505726, dated Mar. 31, 2009.
Kuzuya et al., Report of the Committee on the classification and diagnostic criteria of diabetes mellitus, 55: 65-85, dated Jan. 1, 2002.
Dhar et al., Prognostic significance of metastatic lymph node size in patients with gastric cancer, 90:1522-1530, dated Nov. 3, 2003.
Danne et al., prognostic implications of elevated whole blood choline levels in acute coronary syndromes, 91:1060-67, dated May 1, 2003.
Submitted SNP(ss) details: ss76776255, dated Aug. 28, 2007.
Applied Biosystems, TaqMan SNP genotyping assays protocol, dated Jul. 1, 2010.
Affymetrix, Genome-Wide human SNP Array 6.0, dated Jan. 1, 2009.
Fernandez,Rebollo et al., Intragenic GNAS deletion involving Exon A/B in pseudohypoparahyroidism type 1A resulting in an apparent loss of exon A/B methylation: potential for misdiagnosis of pseudohypoparathyroidism Type 1B, 95(2): 765-771, dated Feb. 1, 2010.
GeneChip assay description from dbSNP, dated Apr. 17, 2017.
Murray et al., genome-wide association of implantable cardioverter-defibrillator activation with life-threatening arrhythmias, vol. 7, issue 1, e25387, dated Jan. 11, 2012.
YefSNP cluster report: rs11856574, dated Apr. 30, 2013.
Kao et al., BACE1 suppresion by RNA interference in primary cortical neurons, vol. 279, No. 3, pp. 1942-1949, dated Nov. 3, 2003.
Xia et al., siRNA-mediated gene silencing in vitro and in vivo, vol. 20, pp. 1006-1011, dated Sep. 16, 2002.
Boillee et al., gene therapy for ALS delivers, vol. 27, No. 5, pp. 235-238, dated May 1, 2004.
Davidson et al., molecular medicine for the brain: silencing of disease genes with RNA interference, 3: 145-149, dated Mar. 1, 2004.
Fu et al., Self-complementary adeno-associated virus serotype 2 vector: global distribution and broad dispersion of AAV-mediated transgene expression in mouse brain, vol. 8, No. 6, pp. 911-917, dated Dec. 1, 2003.
An overview of Illumina's microarrays product used in clinical settings, dated Jan. 1, 2009.
New England Biolabs inc. Catalog p. 121, 264, dated Jan. 1, 1999.
Ahern, biochemical, reagents kits offer scientists good return on investment, 9(15): 20, dated Jul. 24, 1995.
Kidgell et al., elucidating genetic diversity with oligonucleotide arrays, 13, 225-235, dated Jan. 1, 2005.
Gunderson et al., a genome-wide scalable SNP genotyping assay using microarray technology, vol. 37, No. 5, pp. 549-554, dated Apr. 17, 2005.
Yamamoto et al., associationg of a GNAS1 gene variant with hypertension and diabetes mellitus, 27(12): 919-24, dated Dec. 1, 2004.
Chugh et al., genome-wide association study identifies GPC5 as a novel genetic locus protective against sudden cardiac arrest, 6(5): suppl. 1, S142, dated May 1, 2009.
Eijgelsheim et al., identification of a common variant at the NOS1AP locus strongly associated to QT-interval duration, vol. 18, No. 2, pp. 347-357, dated Oct. 16, 2008.
Frey et al., a novel funcitonal haplotype in the human GNAS gene alters Gas expression, responsiveness to b-adrenocepter stimulation, and peri-operative cardiac performance, 30, 1402-10, dated Jan. 10, 2009.
Pearson et al., identification of the genetic basis for complex disorders by use of pooling-based genomewide SNP association studies, vol. 80, pp. 126-139, dated Jan. 1, 2007.
Hapmap: SNP report for rs6565373, dated Oct. 7, 2005.
Birot et al., identification and molecular analysis of BANP, 253, pp. 189-196, dated May 30, 2000.
Weineke et al., polymorphisms associated with ventricular tachyarrhythmias: rationale, design, and endpoints of the diagnostic data influence on disease management and relation of genomics to ventricular tachyarrhythmias in implantable cardioverter/defibrillator patients study, vol. 12, pp. 424-429, dated Feb. 5, 2010.
Gramlich et al., postsynthetic DNA modification through the copper-catalyzed azide-alkyne cycloaddition reaction, vol. 47, pp. 8350-8358, dated Sep. 22, 2009.
Kumar et al., transvascular delivery of small interfering RNA to the central nervous system, nature05901, pp. 1-7, dated Jun. 17, 2007.
Liu et al., brain-targeting gene delivery and cellular internalization mechanisms for modified rabies virus glycoprotein RVG29 nanoparticles, vol. 30, pp. 4195-4202, dated May 20, 2009.
Ilumina introduces Sentrix(R) HumanHap650Y genotyping beadchipl; product sets new standard for SNP density and genomic coverage on a single array; HIV among first areas to be studied, dated Jun. 29, 2006.
RefSNP cluster report: rs5758637, dated Nov. 1, 2003.
RefSNP cluster report: rs151603, dated Nov. 1, 2003.
RefSNP cluster report: rs11196566, dated Nov. 1, 2003.
Hao et al., Calibrating the Performance of SNP arrays for whole-genome association studies, vol. 4, No. 6, https://doi.org/10.1371/journal.pgen.1000109, dated Jun. 27, 2008.
Halushka et al., Patterns of single-nucleotide polymorphisms in candidate genes for blood-pressure homeostasis, vol. 20, pp. 239-247, dated Jul. 1, 1999.
Hattersley et al., What makes a good genetic association study? vol. 366, pp. 1315-1323, dated Oct. 8, 2005.
Ioannidis, Why most published research findings are false, vol. 2, issue 8, pp. 696-701, dated Aug. 1, 2005.

(56) References Cited

OTHER PUBLICATIONS

Pe'er et al., Evaluating and improving power in whole-genome association studies using fixed marker sets, vol. 38, No. 6, pp. 663-667, dated Jun. 1, 2006.
Alizadeh et al.. Distinct types of diffuse large B-cell lymphoma identified by gene expression profiling, vol. 405, pp. 503-511, dated Feb. 3, 2000.
Hirschhorn et al., A comprehensive review of genetic association studies, vol. 4, No. 2, pp. 45-61, dated Mar. 1, 2002.
Ackerman et al., Spectrum and prevalence of cardiac sodium channel variants among black, white, asian, and hispanic individuals: implications for arrhythmogenic susceptibility and Brugada/long QT syndrome genetic testing, 1:600-607, dated Jun. 18, 2004.
Iwasa et al., Twenty single-nucleotide polymorphisms in four genes encoding cardiac ion channels, 47:208-212, dated Jan. 29, 2002.
Josephson et al., implantable defibrillators and sudden cardiac death, 109:2685-91, dated Jan. 1, 2004.
Hegele, SNP judgments and freedom of association, 22:1058-61, dated Jul. 1, 2002.
RefSNP cluster report: rs2072715, dated Nov. 1, 2003.
Sequence revision history for NT_011520, dated Mar. 22, 2010.
Submitted SNP(ss) details: ss7998363, dated May 22, 2012.
2230842-SNP-NCBI, dated Oct. 5, 2012.
Millan et al., using RAPDs to study phylogenetic relationships in Rosa, 92: pp. 273-277, dated Jan. 1, 1996.
Li et al., Comparative genome-scale analysis of gene expression profiles in T Cell lymphoma cells during malignant progression using a complementary DNA microarray, vol. 159, No. 4, pp. 1231-1237, dated Apr. 1, 2001.
Moss et al., Improved survival with an implanted defibrillator in patients with coronary disease at high risk for ventricular arrhythmia, vol. 336, No. 26, pp. 1933-1940, dated Dec. 26, 1996.
Wright et al., Proteinchip surface enhanced laser desorption/ionization mass spectrometry: a novel protein biochip technology for detection of prostate cancer biomarkers in complex protein mixtures, 2: pp. 264-276, dated Dec. 17, 1999.
Albert et al., Prospective study of C-reactive protein, homocysteine, and plsma lipid levels as predictors of sudden cardiac death, 105:2595-99, dated May 13, 2002.
Issaq et al., The SELDI-TOF MS approach to proteomics: protein profiling and biomarker identification, 292, 587-592, dated Feb. 19, 2002.
RefSeq SNP cluster report: rs10505726, dated Apr. 9, 2009.
RefSeq SNP cluster report: rs4878412, dated Apr. 9, 2009.

*1 GICAGCTCCIG
*1 GICAGCTCCIG  ⟶  *1/*1 is CC for 2273 and TT for 2291

*1 GICAGCTCCIG
*3 ADTAATCGCIG  ⟶  *1/*3 is CT for 2273 and TC for 2291

METHODS AND COMPOSITIONS FOR SCD, CRT, CRT-D, OR SCA THERAPY IDENTIFICATION AND/OR SELECTION

CROSS-REFERENCE TO RELATED APPLICATIONS

This application is a divisional of U.S. patent application Ser. No. 14/698,812 filed Apr. 28, 2015, and the disclosure of the above-identified application is hereby incorporated by reference in its entirety.

REFERENCE TO SEQUENCE LISTING

This application contains a Sequence Listing submitted as an electronic text file. The information contained in the Sequence Listing is hereby incorporated herein by reference.

BACKGROUND

Several types of implantable electronic heart devices can be used to treat any one of Sudden Cardiac Arrest (SCA), Sudden Cardiac Death (SCD), or Heart Failure (HF): an Implantable Cardioverter Defibrillator (ICD), a Cardiac Resynchronization Therapy (CRT) pacemaker, or a combination CRT pacemaker that includes defibrillation technology (CRT-D). ICD and CRT-D devices can improve survival as they may be effective in primary and secondary prevention for patients at high risk of Sudden Cardiac Arrest (SCA) or Sudden Cardiac Death (SCD) and can effectively terminate life threatening ventricular tachyarrhythmias, such as ventricular tachycardia (VT) and ventricular fibrillation (VF). For many patients, ICDs are indicated for various cardiac related ailments including myocardial infarction, ischemic heart disease, coronary artery disease, genetic or acquired cardiomyopathies, and heart failure. CRT and CRT-D devices are effective as treatments for patients with heart failure (HF) and/or left ventricular systolic dysfunction (LVSD) and may decrease hospital readmissions, and improve functional status and quality of life in these patient groups.

Ventricular Tachycardia (VT), Ventricular Fibrillation (VF) and SCA/SCD may also be suppressed or treated by the use of pharmacological treatments. These pharmacological treatments are often referred to as anti-arrhythmic drugs (AADs) and are further sub-categorized based on the mechanism of action (e.g., Class I, Class II, and Class III). AADs may be used alone or in combination with ICDs or CRT-Ds. Despite the effectiveness of such therapies in SCA, SCD, HF, or arrest prevention, many patients who might benefit from these therapies do not receive the indicated device or drug due to a lack of reliable methods for the identification of SCD, SCA, or HF risk in susceptible patients. Left ventricular function, clinical comorbidity, QRS duration, and various electrophysiological testing methods have been proposed as criteria for the screening of patients potentially at high risk for arrhythmic death. However, risk stratification remains unsatisfactory as it is mainly performed using a single clinical marker, namely the left ventricular ejection fraction. Not only is this marker imperfect for identifying currently indicated ICD patients, but it excludes a substantial proportion of the population at risk for sudden death who are otherwise asymptomatic.

Many patients who might benefit from an ICD or CRT-D but who are not currently indicated may be identified based on their genetic predisposition. Observational studies suggest that there may be independent genetic contributions to risk of sudden cardiac death. However, exploration of traditional ion channel genes and genome-wide association studies (GWAS) have identified only a small portion of the genetic contribution of SCD. Moreover, a platform does not exist for the combination of one or more diagnostic genetic markers including information about tachyarrhythmia episodes alone or in conjunction with the genetic markers.

There is a need for a genetic basis for risk stratification of patients at risk for any one of SCA, SCD or HF. There is also a need for genetic markers, kits and methods, in silico computer methods as identified herein for identifying patients who can benefit from ICD and CRT-D devices alone or in combination with drug therapy.

SUMMARY OF THE INVENTION

Compositions, polynucleotides, probes, kits, methods, computer systems, and genetic markers useful for assessing the risk of Sudden Cardiac Death (SCD), Sudden Cardiac Arrest (SCA), and Heart Failure (HF) are provided herein. The compositions, polynucleotides, probes, kits, methods, computer systems, and genetic markers of the invention can provide patients selection for those that can be treated with an ICD or CRT-D based on assessing the presence of one or more Single Nucleotide Polymorphisms (SNPs) associated with any one of Ventricular Arrhythmias (VA), Sudden Cardiac Arrest (SCA), Sudden Cardiac Death (SCD), or Heart Failure (HF). In any embodiment, a genetic sample can be assessed for a SNP that is contained in any one of the nucleotide sequences in SEQ ID NO.'s 1-2. In any embodiment, a system of one or more Single Nucleotide Polymorphisms (SNPs) associated with treating a patient at risk for Ventricular Arrhythmias (VA), Sudden Cardiac Arrest (SCA), Sudden Cardiac Death (SCD), or Heart Failure (HF) using anti-arrhythmic drugs (AADs), comprising a computer system, having a computer processor programmed with an algorithm, and one or more genetic databases that are in communication with the programmed processor. In any embodiment, a programmed computer processor can be used to diagnose a patient for any of the described conditions or therapies, and/or impute p-values for one or more known SNPs detected in DNA contained in one or more genetic samples obtained from a patient and/or from the one or more genetic databases.

The first aspect of the invention is drawn to an isolated nucleic acid molecule for treating a patient with anti-arrhythmic drugs (AADs) wherein the patient has Ventricular Arrhythmias (VA), Sudden Cardiac Arrest (SCA), Sudden Cardiac Death (SCD), or Heart Failure (HF). The patient can have a Single Nucleotide Polymorphism (SNP) contained in any one of the nucleotide sequences in SEQ ID NO.'s 1-2. The isolated nucleic acid can overlap a polymorphic position in any one of SEQ ID NO.'s 1-2.

The second aspect of the invention is drawn to diagnostic kits and methods for assessing the risk of VA, SCD, SCA, or HF using genetic markers thereof are provided having at least one probe for assessing the presence of one or more Single Nucleotide Polymorphisms (SNPs) associated with any one of VA, Sudden Cardiac Arrest (SCA), Sudden Cardiac Death (SCD), or Heart Failure (HF) in a genetic sample wherein the SNP is contained in any one of the nucleotide sequences in SEQ ID NO.'s 1-2.

The third aspect of the invention is drawn to a companion diagnostic for treating a patient with anti-arrhythmic drugs (AADs) or biologic therapies having VA, Sudden Cardiac Arrest (SCA), Sudden Cardiac Death (SCD), or Heart Failure (HF) wherein the SNP is contained in any one of the nucleotide sequences in SEQ ID NO.'s 1-2 is contemplated by the invention.

The fourth aspect of the invention is drawn to methods of distinguishing patients having an increased susceptibility to VA, SCD, SCA, or HF using the diagnostic kits and methods, including various DNA microarrays, in silico computer methods through use of the genetic markers, alone or in combination with other markers, are also provided wherein at least one probe for assessing the presence of one or more Single Nucleotide Polymorphisms (SNPs) associated with any one of VA, Sudden Cardiac Arrest (SCA), Sudden Cardiac Death (SCD), or Heart Failure (HF) in a genetic sample wherein the SNP is contained in any one of the nucleotide sequences in SEQ ID NO.'s 1-2.

The DNA microarrays can be in situ synthesized oligonucleotides, randomly or non-randomly assembled bead-based arrays, and mechanically assembled arrays of spotted material where the materials can be an oligonucleotide, a cDNA clone, or a Polymerase Chain Reaction (PCR) amplicon.

Specifically, a diagnostic kit for detecting one or more VA, SCA, SCD or HF-associated polymorphisms in a genetic sample having at least one probe for assessing the presence of a Single Nucleotide Polymorphism (SNP) in any one of SEQ ID NO.'s 1-2 is provided. Also provided is a DNA microarray for detecting one or more SCA, SCD or HF-associated polymorphisms in a genetic sample made up of at least one probe for assessing the presence of a Single Nucleotide Polymorphism (SNP) in any one of SEQ ID NO.'s 1-2.

The first, second, third and fourth aspects of the invention contemplate a diagnostic kit for detecting one or more Single Nucleotide Polymorphisms (SNPs) associated with VA, SCA, SCD or HF that is treatable with a CRT-D or ICD, comprising at least one probe that is used for assessing the presence of said one or more SNPs in a genetic sample, the SNPs being selected from any one of the following sequences:

tides or complements thereof can be from about 15 to 101, 17 to 101, 19 to 101, 21 to 101, 24 to 101, 26 to 101, nucleotides in length, or 15 to 50, 17 to 50, 19 to 50, 21 to 50, 24 to 50, 26 to 50 nucleotides in length, and so forth. Both the major or minor allele can be probed.

In any of the first, second, third or fourth aspects of the invention, the SNP can be bi-allelic or multi-allelic. The complement can be an allele-specific probe or primer.

Preferred primer lengths can be from 25 to 35, 18 to 30, 17 to 24, 15 to 101, 17 to 101, 19 to 101, 21 to 101, 24 to 101, 26 to 101, 15 to 50, 17 to 50, 19 to 50, 21 to 50, 24 to 50, and 26 to 50 nucleotides. A preferred length is 52 nucleotides with the polymorphism at position 26 or 27. An amplified nucleotide is further contemplated containing a SNP embodied in any one of SEQ ID NO.'s 1-2, or a complement thereof, overlapping the polymorphic position, wherein the amplified nucleotide is between 12 and 101 base pairs in length described by n for the lower bound, and (n+i) for the upper bound for n=$\{x \in \mathbb{R} \mid 12 < x \leq 101\}$ and i=$\{y \in \mathbb{R} \mid 0 \leq y \leq (101-n)\}$. The lower limit of the number of nucleotides in the isolated nucleotides, and complements thereof, can range from about 12 base pairs from position 26 to 28 in any one of SEQ ID NO.'s 1-2 such that the polymorphic position is flanked on either the 5' and 3' side by a single base pair, to any number of base pairs flanking the 5' and 3' side of the SNP sufficient to adequately identify, or result in hybridization. The lower limit of nucleotides can be from about 12 to 101 base pairs described by n for the lower bound, and (n+i) for the upper bound for n=$\{x \in \mathbb{R} \mid 12 < x \leq 101\}$ and i=$\{y \in \mathbb{R} \mid 0 \leq y \leq (101-n)\}$, the optimal length being determinable by a person of ordinary skill in the art. It is also understood that the optimal length determined by one of ordinary skill in the art may exceed 101 base pairs.

In any of the first, second, third or fourth aspects of the invention the probe can be detected by any of electrical, fluorescent or radioactive means. An amplified DNA sample can be labeled with a detectable label. The probe can be immobilized to a solid support. The presence of hybridiza-

| SNP | FASTA allele | SEQ ID No. | S number |
|---|---|---|---|
| c.393 C < T | agaaccagttcagagtggactacat[c/t]ctgagtgtgatgaacgtgcctgact | (SEQ ID No. 1) | rs7121 |
| c.2273 C < T | ttgcctctggcctaggaatctgcag[c/t]ttaagccagtgacacaatattttgc | (SEQ ID No. 2) | rs12481583 |

Also contemplated by the first, second, third and fourth aspects of the invention are polynucleotides comprising a complement of any length sufficient for identification of a nucleotide sequence having a Single Nucleotide Polymorphism (SNP) selected from any one of SEQ ID NO.'s 1-2 for either the major or minor allele where the complement is between from about 12 to 101 nucleotides in length, flanks the polymorphic position on either the 5' or 3' side, and overlaps a polymorphic position in any of the SEQ ID NO.'s 1-2, representing a SNP. In particular, the nucleotide lengths can be described by n for the lower bound, and (n+i) for the upper bound for n=$\{x \in \mathbb{R} \mid 12 < x \leq 101\}$ and i=$\{y \in \mathbb{R} \mid 0 \leq y \leq (101-n)\}$. For example, the isolated nucleotides or complements thereof, can be for n=12, for every i=$\{y \in \mathbb{R} \mid 0 \leq y \leq (89)$ from about 12 to 13 nucleotides in length, or from about 12 to 14, 12 to 15, 12 to 17, 12 to 18, . . . , 12 to 99, 12 to 100, 12 to 101, so long as the polymorphic position in any of SEQ ID NO.'s 1-2 is overlapped. Similarly, the isolated nucleotion can be determined by detecting the location of the detectable label on the solid support by any of spectroscopic, photochemical, biochemical, immunochemical, electrical, optical, and chemical means.

In any of the first, second, third or fourth aspects of the invention, the SNP can comprise at least one of a TT genotype of subunit C393T of the GNAS gene and the TT genotype of subunit C2273T of the GNAS gene.

The fifth aspect of the invention contemplate a system for detecting one or more Single Nucleotide Polymorphisms (SNPs) associated with VA, SCA, SCD, or HF that is treatable with a CRT-D or ICD, comprising a computer system, having a computer processor programmed with a MACH algorithm, and one or more genetic databases that are in communication with the programmed computer processor, wherein the programmed computer processor is used to impute p-values for one or more known SNPs detected in DNA contained in one or more genetic samples obtained from a patient and/or from the one or more genetic databases, and wherein low p-values indicate an association with VA, SCA, SCD, or HF that is treatable with a CRT-D or ICD.

The sixth aspect of the invention contemplates an isolated nucleic acid molecule useful for predicting VA, SCA, SCD, or HF that is treatable with a CRT-D or ICD, comprising a nucleotide sequence having a Single Nucleotide Polymorphism (SNP).

The seventh aspect of the invention contemplates a method of distinguishing one or more patients as having an increased or decreased susceptibility to SCA, SCD, or HF treatable with a CRT-D or ICD, comprising the step of imputing p-values for one or more known SNPs detected in DNA contained in one or more genetic samples obtained from a patient and/or from the one or more genetic databases, and wherein p-values below a threshold value of alpha (i.e., alpha=0.05 or 0.01), which can be controlled for multiple comparisons (i.e., Bonferroni correction), indicate increased susceptibility to VA, SCA, SCD, OR HF that is treatable with an CRT-D or ICD.

The eight aspect of the invention contemplates a method of detecting a polymorphism associated with VA, SCA, SCD, or HF that is treatable with a CRT-D or ICD, comprising the steps of extracting genetic material from a biological sample and screening said genetic material for at least one Single Nucleotide Polymorphism (SNP) in any of SEQ ID NO.'s 1-2.

The ninth aspect of the invention contemplates a method of distinguishing one or more patients as having an increased or decreased susceptibility to VA, SCA, SCD, or HF treatable with a CRT-D or ICD, comprising the steps of determining the presence or absence of at least one Single Nucleotide Polymorphism (SNP) in any one of SEQ ID NO.'s 1-2 in a nucleic acid sample obtained from said one or more patients and assessing susceptibility to SCA based on the determination.

The tenth aspect of the invention contemplates a polynucleotide useful for predicting VA, SCA, SCD, or HF that is treatable with a CRT-D or ICD, comprising a nucleotide sequence having a Single Nucleotide Polymorphism (SNP) at a polymorphic position in any one of SEQ ID NO.'s 1-2.

The eleventh aspect of the invention contemplates an amplified polynucleotide containing a Single Nucleotide Polymorphism (SNP) selected from SEQ ID NO.'s 1-2, or a complement thereof. The invention contemplates a DNA microarray for determining the presence or absence one or more polymorphisms associated with VA, SCA, SCD, or HF that is treatable with a CRT-D or ICD in a genetic sample, comprising at least one probe for detecting a Single Nucleotide Polymorphism (SNP) in any one of SEQ ID NO.'s 1-2.

The twelfth aspect of the invention contemplates a method of determining a risk score for one or more patients as having an increased or decreased susceptibility to VA, SCA, SCD, or HF where the presence or absence of at least one Single Nucleotide Polymorphism (SNP) in any one of SEQ ID NO.'s 1-2 in a nucleic acid sample obtained from said one or more patients is determined, and the number of minor alleles is then determined, and then the increased or decreased susceptibility to SCA is assessed based on the determinations. The invention also contemplates a method of determining a risk score for one or more patients as having an increased or decreased susceptibility to VA, SCA, SCD, or HF based on if SEQ ID NO.'s 1-2 are in high linkage disequilibrium within a haplotype block in a nucleic acid sample obtained from said one or more patients.

The thirteenth aspect of the invention contemplates methods for identifying and/or treating patients who are not on optimal candidate for beta-blocker therapy and who may have a higher risk of CRT non-response. Those skilled in the art will recognize that the analysis of the nucleotides present in one or several of the SNP markers in an individual's nucleic acid can be done by any method or technique capable of determining nucleotides present at a polymorphic site. One of skill in the art would also know that the nucleotides present in SNP markers can be determined from either nucleic acid strand or from both strands.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

BRIEF DESCRIPTION OF THE DRAWINGS

The foregoing and other features and aspects of the present disclosure will be best understood with reference to the following detailed description of a specific embodiment of the disclosure, when read in conjunction with the accompanying drawings, wherein.

DETAILED DESCRIPTION OF THE INVENTION

Figure 1:
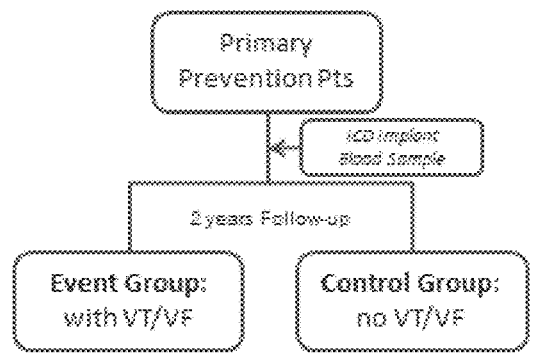
FIG. 1 is a flow chart of the DISCOVERY study design.

The first through thirteenth aspects of the invention relate to compositions, polynucleotides, probes, kits, methods, computer systems, and genetic markers using a nucleic acid molecule to predict Ventricular Arrhythmias (VA), Sudden Cardiac Death (SCD), Sudden Cardiac Arrest (SCA), and Heart Failure (HF), the nucleic acid molecule having a Single Nucleotide Polymorphism (SNP) in any one of SEQ ID NO.'s 1-2 that can be used in the diagnosis, distinguishing, and detecting of susceptibility to VA, SCD, SCA, or HF that can be treated with known pharmacological, biologic, or device therapies to prevent, suppress or treat VA, SCD, SCA, or HF, such as CRT-D or ICD.

Definitions

Unless defined otherwise, all technical and scientific terms used herein have the same meaning as commonly understood by one of ordinary skill in the art to which this invention belongs. For purposes of the present invention, the following terms are defined below.

The terms "a," "an," and "the" include plural referents unless the context clearly dictates otherwise.

The phrase, "affixed to a substrate," refers to the process of attaching probes of DNA to a substrate so that a target sample is bound or hybridized with the probes. The surface of the substrate is chemically prepared or derivatized to enable or facilitate the attachment or affixment of the molecular species to the surface of the array substrate. This process is described in detail below.

"Allele" is one of two or more alternate forms of a gene occupying the same locus in a particular chromosome or linkage structure and differing from other alleles of the locus at one or more mutational sites. Rieger et al., GLOSSARY OF GENETICS, 5TH ED., Springer-Verlag, Berlin 1991; 16.

Allele Specific Oligomer ("ASO") refers to a primary oligonucleotide having a target specific portion and a target-identifying portion, which can query the identity of an allele at a SNP locus. The target specific portion of the ASO of a primary group can hybridize adjacent to the target specific portion and can be made by methods well known to those of ordinary skill.

The term "amplified polynucleotide" or "amplified nucleotide" as used herein refers to polynucleotides or nucleotides that are copies of a portion of a particular polynucleotide sequence and/or its complementary sequence, which correspond to a template polynucleotide sequence and its complementary sequence. An "amplified polynucleotide" or "amplified nucleotide" according to the present invention may be DNA or RNA, and it may be double-stranded or single-stranded.

An "antisense" strand is the one strand that codes in double-stranded DNA for the RNA that is translated into protein. The strand that does not code for RNA is called the "sense" strand. The antisense DNA is the strand that carries the information necessary to make proteins by binding to a corresponding messenger RNA (mRNA). Although both the antisense and sense strands are mirror images of one another, only the antisense strand contains the information for making proteins.

"Antisense compounds" are oligomeric compounds that are at least partially complementary to a target nucleic acid molecule to which they hybridize. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

The phrase "assessing the presence" of one or more SNPs in a genetic sample encompasses any known process that can be implemented to determine if a polymorphism is present in a genetic sample. For example, amplified DNA obtained from a genetic sample can be labeled before it is hybridized to a probe on a solid support. The amplified DNA is hybridized to probes which are immobilized to known locations on a solid support, e.g., in an array, microarray, high density array, beads or microtiter dish. The presence of labeled amplified DNA products hybridized to the solid support indicates that the nucleic acid sample contains at the polymorphic locus a nucleotide which is indicative of the polymorphism. The quantities of the label at distinct locations on the solid support can be compared, and the genotype can be determined for the sample from which the DNA was obtained. Two or more pairs of primers can be used for determining the genotype of a sample. Each pair of primers specifically amplifies a different allele possible at a given SNP. Further, it will be understood that "assessing" encompassing any method known to those of skill in the art sufficient to identify a SNP or result in identification whether by hybridization of a probe such that there is sufficient specificity and sensitivity to detect and identify a SNP sequence or result in a hybridization, or an electronic algorithmic scan of an existing genomic database to determine whether the SNP is present in the database. The optimal probe length, position, and number of probes for detection of the SNP for hybridization or the optimal algorithm for an electronic interrogation of a genetic database may vary depending on various requirements for identification of the SNP.

"Bi-allelic" and "multi-allelic" refer to two, or more than two alternate forms of a SNP, respectively, occupying the same locus in a particular chromosome or linkage structure and differing from other alleles of the locus at a polymorphic site.

The terms "biologic therapy" or "biological therapy" refer to therapies that cause a patient's body to fight a disease. In any embodiment, biologic therapy can refer to the use of gene therapy to modify a disease-causing gene, or to introduce a new gene into a patient that provides protection against a disease.

The term "companion diagnostic" refers to a biomarker such as a SNP, molecular assays measuring levels of proteins, genes, or specific mutations, or any diagnostic used to provide information if a patient can respond or not respond to a therapy for the patient's condition.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

The term "contigs" is an abbreviation of the word "contiguous," used herein to describe a set of overlapping DNA segments that together represent a consensus region of DNA.

The terms "Cardiac Resynchronization Therapy," "CRT pacemaker," "CRT device," collectively refer to medical devices and therapies for bi-ventricular pacing to help improve a heart's rhythm and the symptoms associated with heart failure. In general, the terms refer to coordinating the pumping of the two ventricles to improve heart efficiency in heart failure patients.

A "CRT-D" is device having both a defibrillator such as an Implantable Cardioverter Defibrillator (ICD) and a CRT device.

The term "detecting" is used to describe any known process for detection. For example, nucleic acids can be detected by hybridization, observation of one or more labels attached to target nucleic acids, or any other convenient means known to those of ordinary skill. A label can be incorporated by labeling the amplified DNA product using a terminal transferase and a fluorescently labeled nucleotide. Useful detectable labels include labels that can be detected by spectroscopic, photochemical, biochemical, immunochemical, electrical, optical, or chemical means. Radioactive labels can be detected using photographic film or scintillation counters. Fluorescent labels can be detected using a photodetector.

The term "detecting" as used in the phrase "detecting one or more Single Nucleotide Polymorphisms (SNPs)" refers to any suitable method for determining the identity of a nucleotide at a position including, but not limited to, sequencing, allele specific hybridization, primer specific extension, oligonucleotide ligation assay, restriction enzyme site analysis and single-stranded conformation polymorphism analysis.

A "diagnostic kit" means any medical device which is a reagent, reagent product, calibrator, control material, kit, instrument, apparatus, equipment, or system, whether used alone or in combination, that is used for the examination of specimens, including blood and tissue donations, genetic samples, derived from a patient, solely or principally for the purpose of providing information about a physiological or pathological state, or concerning a congenital abnormality, or to determine the safety and compatibility with potential recipients, or to monitor therapeutic measures. The specific "diagnostic kits" of the invention are defined more fully herein.

The term "extracting" information or genetic material broadly encompasses any process by which genetic information such as nucleotide sequence, polymorphism or other characteristic of the genetic material can be observed and processed into information either electronic, analog, or other form by any means known to those of ordinary skill in the art.

The term "Hidden Markov Model (HMM)" describes a statistical method for determining a state, which has not been observed or "hidden." The HMM is generally based on a Markov chain, which describes a series of observations in which the probability of an observation depends on a number of previous observations. For a HMM, the Markov process itself cannot be observed, but only the steps in the sequence.

As used herein, "hybridization" is defined as the ability of two nucleotide sequences to bind with each other based on a degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. Stringent conditions are conditions under which a probe can hybridize to its target subsequence, but to no other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide or tetra alkyl ammonium salts. For example, conditions of 5xSSPE (750 mM NaCl, 50 mM Na Phosphate, 5 mM EDTA, pH 7.4) and a temperature of 25-30° C. are suitable for allele-specific probe hybridizations. Sambrook et al., MOLECULAR CLONING, 1989.

An Implantable Cardioverter Defibrillator (ICD) is a small battery-powered electrical impulse generator implanted in patients who are at risk of sudden cardiac death due to ventricular fibrillation and/or ventricular tachycardia. The device is programmed to detect cardiac arrhythmia and treat the arrhythmia via the delivery of electrical energy or anti-tachycardia pacing. Electrical energy may be low voltage (for instance, pacing therapy) or high voltage (for instance, shock), or a combination thereof. Cardiac arrhythmias include both atrial and ventricular arrhythmias, including those cardiac rhythms which are too slow (bradyarrhythmias) or too fast (tachyarrhythmias). An ICD may have the ability to deliver both atrial and ventricular therapies for treating cardiac arrhythmias and may also include the ability to deliver biventricular pacing (similar to a standalone CRT) in patients with congestive heart failure.

As used herein, to "impute a p-value to one or more SNPs outside of a test sample" means to mathematically attribute a p-value to one or more known and documented SNPs, using the methods described herein, that are not present on the test microchips used in a specific experiment or study. Using the p-values obtained from the tested microchips, p-values may be mathematically imputed to other known SNPs using an "algorithm" or "algorithms" such as those described herein.

By the phrase, "in communication," it is meant that the elements of the system of the invention are so connected, either directly or remotely, that data can be communicated among and between said elements.

The phrases "increased susceptibility," "decreased susceptibility," or the term "risk," generally, relates to the possibility or probability of a particular event occurring either presently or at some point in the future. Determining an increase or decrease in susceptibility to a medical disease, disorder or condition involves "risk stratification" or "assessing susceptibility," which refers to an analysis of known clinical risk factors that allows physicians and others of skill in the relevant art to classify patients from a low to high range of risk of developing a particular disease, disorder, or condition.

By the phrase "indicate association" or "associated with," it is meant that statistical analysis suggests, by, for example, a p-value, that a SNP may be linked to a particular medical disease, condition, or disorder.

The term "isolated" refers to nucleic acid, or a fragment thereof, that has been removed from its natural cellular environment. The term "isolated" as used herein with reference to a nucleic acid molecule refers to a nucleic acid that is not immediately contiguous with both of the sequences with which it is immediately contiguous in the naturally occurring genome of the organism from which it is derived. The term "isolated" also includes any non-naturally occurring nucleic acid because such engineered or artificial nucleic acid molecules do not have immediately contiguous sequences in a naturally occurring genome.

"Genetic database" refers generally to a database containing genetic sequence information.

The term "genetic material" and/or "genetic sample" refers to a nucleic acid sequence that is sought to be obtained from any number of sources, including, without limitation, whole blood, a tissue biopsy, lymph, bone marrow, hair, skin, saliva, buccal swabs, purified samples generally, cultured cells, and lysed cells, and can comprise any number of different compositional components (e.g., DNA, RNA, tRNA, siRNA, mRNA, or various non-coding RNAs). The nucleic acid can be isolated from samples using any of a variety of procedures known in the art. In general, the target nucleic acid will be single stranded, though in any embodiments the nucleic acid can be double stranded, and a single strand can result from denaturation. It will be appreciated that either strand of a double-stranded molecule can serve as a target nucleic acid to be obtained. The nucleic acid sequence can be methylated, non-methylated, or both and can contain any number of modifications. Further, the nucleic acid sequence can refer to amplification products as well as to the native sequences.

The term "MACH" or "MACH 1.0" refers to a haplotyper program using a Hidden Markov Model (HMM) that can resolve long haplotypes or infer missing genotypes in samples of unrelated individuals as known within the art.

A "major allele" is defined as a more common nucleotide or an allele having a greater frequency in comparison to other alleles. A "minor allele" is a less common nucleotide or an allele having a lesser frequency.

"Mutations" are changes in a genomic sequence. As used herein, "naturally occurring mutants" refers to any preexisting, not artificially induced change in a genomic sequence. Mutations, mutant sequences, or, simply, "mutants" include additions, deletions and substitutions or one or more alleles.

The term "nucleic acid" refers to a deoxyribonucleotide or ribonucleotide polymer in either single- or double-stranded form, and, unless otherwise limited, encompasses known analogues of natural nucleotides that hybridize to nucleic acids in a manner similar to naturally occurring nucleotides. The term "nucleic acid" encompasses the terms "oligonucleotide" and "polynucleotide."

In statistical significance testing, the "p-value" is the probability of obtaining a test statistic at least as extreme as the one that was actually observed, assuming that the null hypothesis is true. The lower the p-value, the less likely the result is if the null hypothesis is true, and consequently the more "significant" the result is, in the sense of statistical significance. A "low p-value" as described herein is a value below an alpha value (i.e., alpha=0.05 or 0.01) that can be controlled for multiple comparisons (i.e., Bonferroni correction).

"Pharmacological therapy" refers to the treatment of a disease by introducing one or more drugs into a patient.

The term "plurality" as described herein means more than one, and also defines a multiple of items.

A "polymorphic position" or "polymorphic site" is defined as a position in a nucleotide wherein a single nucleotide differs between other nucleotides within a population or paired chromosomes as shown herein.

As used herein, the term "primer pair" means two oligonucleotides designed to flank a region of a polynucleotide to be amplified.

"Probes" or "primers" refer to single-stranded nucleic acid sequences that are complementary to a desired target nucleic acid. The 5' and 3' regions flanking the target complement sequence reversibly interact by means of either complementary nucleic acid sequences or by attached members of another affinity pair. Hybridization can occur in a base-specific manner where the primer or probe sequence is not required to be perfectly complementary to all of the sequences of a template. Hence, non-complementary bases or modified bases can be interspersed into the primer or probe, provided that base substitutions do not inhibit hybridization. The nucleic acid template may also include "non-specific priming sequences" or "nonspecific sequences" to which the primers or probes have varying degrees of complementarity. As used in the phrase "priming polynucleotide synthesis," a probe is described that is of sufficient length to initiate synthesis during PCR. In any embodiments, a probe or primer can comprise 101 or fewer nucleotides, wherein the length of the complement is described by a length for the lower bound, and (n+i) for the upper bound for $n=\{x \in \mathbb{R} \mid 0 < x \leq 101\}$ and $i=\{y \in \mathbb{R} \mid 0 \leq y \leq (101-n)\}$, or from about any number of base pairs flanking the 5' and 3' side of a region of interest to sufficiently identify, or result in hybridization. Further, the ranges can be chosen from group A and B, where for A, the probe or primer is greater than 5, greater than 10, greater than 15, greater than 20, greater than 25, greater than 30, greater than 40, greater than 50, greater than 60, greater than 70, greater than 80, greater than 90 and greater than 100 base pairs in length. For B, the probe or primer is less than 102, less than 95, less than 90, less than 85, less than 80, less than 75, less than 70, less than 65, less than 60, less than 55, less than 50, less than 45, less than 40, less than 35, less than 30, less than 25, less than 20, less than 15, or less than 10 base pairs in length. In any embodiment, the probe or primer can be at least 70% identical to the contiguous nucleic acid sequence or to the complement of the contiguous nucleotide sequence, for example, at least 80% identical, at least 90% identical, at least 95% identical, and is capable of selectively hybridizing to the contiguous nucleic acid sequence or to the complement of the contiguous nucleotide sequence. Preferred primer lengths include 25 to 35, 18 to 30, and 17 to 24 nucleotides. Often, the probe or primer further comprises a "label," e.g., radioisotope, fluorescent compound, enzyme, or enzyme co-factor. One primer is complementary to nucleotides present on the sense strand at one end of a polynucleotide to be amplified and another primer is complementary to nucleotides present on the antisense strand at the other end of the polynucleotide to be amplified. The polynucleotide to be amplified can be referred to as the template polynucleotide. The nucleotides of a polynucleotide to which a primer is complementary is referred to as a target sequence. A primer can have at least about 15 nucleotides, preferably, at least about 20 nucleotides, most preferably, at least about 25 nucleotides. Typically, a primer has at least about 95% sequence identity, preferably at least about 97% sequence identity, most preferably, about 100% sequence identity with the target sequence to which the primer hybridizes. The conditions for amplifying a polynucleotide by PCR vary depending on the nucleotide sequence of primers used, and methods for determining such conditions are routine in the art. To obtain high quality primers, primer length, melting temperature ($T_m$), GC content, specificity, and intra- or inter-primer homology are taken into account in the present invention. You et al., BatchPrimer3: A high throughput web application for PCR and sequencing primer design, BMC BIOINFORMATICS, 2008; 9:253; Yang X., Scheffler B E, Weston L A, Recent developments in primer design for DNA polymorphism and mRNA profiling in higher plants, PLANT METHODS, 2006; 2(1):4. Primer specificity is related to primer length and the final 8 to 10 bases of the 3' end sequence where a primer length of 18 to 30 bases is one possible embodiment. Abd-Elsalam K A, Bioinformatics tools and guideline for PCR primer design, AFRICA J. OF BIOTECHNOLOGY 2003; 2(5): 91-95. $T_m$ is closely correlated to primer length, GC content and primer base composition. One possible ideal primer $T_m$ is in the range of 50 to 65° C. with GC content in the range of 40 to 60% for standard primer pairs. Dieffenbatch C W, Lowe T M J, Dveksler G S, General concepts for PCR primer design, PCR PRIMER, A LABORATORY MANUAL, Eds: Dieffenbatch C W, Dveksler G S, New York, Cold Spring Harbor Laboratory Press, 1995; 133-155. However, the optimal primer length varies depending on different types of primers. For example, SNP genotyping primers may require a longer primer length of 25 to 35 bases to enhance their specificity, and thus the corresponding $T_m$ might be higher than 65° C. Also, a suitable $T_m$ can be obtained by setting a broader GC content range (20 to 80%).

The terms "processor" and "computer processor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In any embodiment, the terms can include ROM ("read-only memory") and/or RAM ("random-access memory") associated therewith.

"Polynucleotide probes," "Anti sense nucleic acid primers" "oligonucleotide probes," refer to probes or primers that can be constructed using chemical synthesis and enzymatic ligation reactions known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids. The primers or probes can further be used in "Polymerase Chain Reaction" (PCR), a well-known amplification and analytical technique that generally uses two "primers" of short, single-stranded DNA synthesized to correspond to the beginning of a DNA stretch to be copied, and a polymerase enzyme that moves along the segment of DNA to be copied that assembles the DNA copy.

As used herein, a "risk score" is defined as a predisposition to a condition. Generally, a risk can be expressed as a percentage for an indication of the likeliness of the chance event, such as a medically defined phenotype, such as a condition or a non-medical phenotype, such as a trait, to occur. "Risk scores" can be provided with a confidence interval, a statistical value such as a p-value, Z-score, correlation (e.g., R or R2), chi-square, f-value, t-value or both a confidence interval and a statistical value, indicating the strength of correlation between the score and the condition or trait thereof. Scores can be generated for an individual's risks or predispositions for medical conditions based on an individual's genetic profile. Scores can be determined for a specific phenotype (e.g., disease, disorder, condition or trait), for an organ system, for a specific organ, for a combination of phenotypes for a combination of phenotype(s) and organ(s) or organ system(s), for overall health, or for overall genetic predisposition to or risk of specific phenotypes. The phenotype may be a medical condition, for example, scores can be generated for an individual's risks or predispositions for medical conditions based on an individual's genetic profile. Alternatively, scores can be for non-medical conditions, or for both medical and non-medical conditions. Scores may be generated by methods known in the arts, such as described in PCT Publication WO2008/067551 and U.S. Publication No. 20080131887 (each of which is incorporated herein by reference in its entirety) methods such as described herein, or variations and combinations thereof. In some cases, the risks may be determined using a special purpose computer using instructions provided on computer readable medium. Inclusion of the specific algorithms described herein to analyze the genetic information and calculate scores representing risks, predisposition to a phenotype and/or overall health profiles, for example, transform a general-purpose computer into a special purpose computer for analyzing the genetic variants identified. Such algorithms can be provided in any combination to execute those functions desired by a client. Thus, the computer system may include some or all of the computer executable logic encoded on computer readable medium to instruct the computer system to complete the analysis, evaluations, scoring of the identified genetic variants, recommendations and reports for the client as desired. As used herein, a calculated or determined risk or predisposition of one or more specific phenotypes from an individual's genetic profile provides a measure of the relative risk or predisposition of that individual for one or more phenotypes, as further described herein. The relative risk may be determined as compared to the general population or as compared to a control (e.g., a different individual) lacking one or more of the genetic variants identified in the individual's genetic profile. In some cases, an individual with a decreased risk or decreased predisposition for a specific phenotype is an individual with an odds ratio of less than 1, for example 0.99, 0.9, 0.8, 0.7, 0.5, 0.4, 0.2, 0.1, 0.01 or lower odds ratio relative to a control individual or relative to the general population. An individual with a decreased risk or predisposition for a specific phenotype may be an individual with a lower percentage probability than a control individual or the general population for a phenotype. For example, in any embodiment of the present invention, an individual may have a 0.1% lower risk, 1% lower risk, 5% lower risk, 10% lower risk, 15% lower risk, 25% lower risk, 30% lower risk, 40% lower risk, 50% lower risk, 75% lower risk, or 100% lower risk than a control individual or the general population for a phenotype. An individual's decreased risk or predisposition may also be determined as a hazard ratio or a relative risk.

An "rs number" refers to a SNP database record archived and curated on dbSNP, which is a database for Single Polymorphism Polynucleotides and Other Classes of Minor Genetic Variations. The dbSNP database maintains two types of records: ss records of each original submission and rs records. The ss records may represent variations in submissions for the same genome location. The rs numbers represent a unique record for a SNP and are constructed and periodically reconstructed based on subsequent submissions and Builds of a database. In each new Build cycle, the set of new data entering each Build typically includes all submissions received since the close of data in the previous Build. Some ref SNP (rs) numbers might have been merged if they are found to map the same location at a later build, however, it is understood that a particular rs number with a Build number provides the requisite detail so that one of ordinary skill in the art will be able to make and use the invention as contemplated herein. Hence, one of ordinary skill will generally be able to determine a particular SNP by reviewing the entries for an rs number and related ss numbers. Data submitted to the NCBI database are clustered and provide a non-redundant set of variations for each organism in the database. The clusters are maintained as rs numbers in the database in parallel to the underlying submitted data. Reference Sequences, or RefSeqs, are a curated, non-redundant set of records for mRNAs, proteins, contigs, and gene regions constructed from a GenBank exemplar for that protein or sequence. The accession numbers under "Submitter-Referenced Accessions" is annotation that is included with a submitted SNP (ss) when it is submitted to dbSNP (Sherry et al., *dbSNP—Database for Single Polymorphism Polynucleotides and Other Classes of Minor Genetic Variation,* GENOME RES. 1999; 9: 677-679). However, other alternate forms of the rs number as provided in RefSeq, ss numbers, etc. are contemplated by the invention such that one of ordinary skill in the art would understand that the scope and nature of the invention is not departed by using follow-on builds of dbSNP.

The term "screening" within the phrase "screening for a genetic sample" means any testing procedure known to those of ordinary skill in the art to determine the genetic make-up of a genetic sample.

The term "single nucleotide polymorphisms" (SNPs) refers to a variation in the sequence of a gene in the genome of a population that arises as the result of a single base change, such as an insertion, deletion or, a change in a single base. A locus is the site at which divergence occurs. SNPs can further be defined as single base exchanges occurring in over 1% of the population. SNPs can result in modified amino acid sequences, altering structure and function of coded protein, and influence the splicing process when present at exon-intron transitions and modify gene transcription when part of promoters. This modification can lead to altered levels of protein expression.

The phrase "sufficient to identify the SNP or result in a hybridization" is understood to encompass design and use of probes such that there is sufficient specificity and sensitivity to detect and identify a SNP sequence or result in a hybridization. The optimal probe length, position, and number of probes for detection of a single nucleotide polymorphism or for hybridization may vary depending on various hybridization conditions.

"Synthesis" and "amplification" as used herein are used interchangeably to refer to a reaction for generating a copy of a particular polynucleotide sequence or increasing in copy number or amount of a particular polynucleotide sequence. It may be accomplished, without limitation, by the in vitro methods of polymerase chain reaction (PCR), ligase chain reaction (LCR), polynucleotide-specific based amplification (NSBA), or any other method known in the art. For example, polynucleotide amplification may be a process using a polymerase and a pair of oligonucleotide primers for producing any particular polynucleotide sequence, i.e., the target polynucleotide sequence or target polynucleotide, in an amount which is greater than that initially present.

The phrase "selectively hybridizing" refers to the ability of a probe used in the invention to hybridize, with a target nucleotide sequence with specificity.

The term "treatable" means that a patient is potentially or would be expected to be responsive to a particular form of treatment.

Diagnostic and Therapeutic Uses of SNPs

In some cases, an individual with an increased relative risk or predisposition for a specific phenotype may be an individual with an odds ratio of greater than 1 for the specific phenotype, for example an individual can be diagnosed with an odds ratio of about 1.01, 1.05, 1.1, 1.2, 1.5, 2, 2.5, 3, 4, 5, 6, 7, 8, 9, 10, 15, 20, 25, 50, or 100 or more for developing a phenotype relative to the general population or a control individual. In some cases, an individual with an increased risk or predisposition may be an individual with a greater than 0% increased probability of a phenotype, for example an individual may have a 0.001% greater probability of a phenotype based on their genetic profile, a 0.01% greater probability, a 1% greater probability, a 5% greater probability, a 10% greater probability, a 20% greater probability, a 30% greater probability, a 50% greater probability, a 75% greater probability, a 100% greater probability, a 200%, 300%, 400%, 500% or more greater probability of a phenotype relative to the general population or a control individual. In some cases, an individual with an increased risk or predisposition may be an individual with a greater than 1 fold increased probability of a phenotype relative to a control individual or the general population such as for example about a 1.01 fold, 1.1 fold, 1.2 fold, 1.3 fold, 1.4 fold, 1.5 fold, 2 fold, 3 fold, 5 fold, 10 fold, 100 fold or more increased probability of a phenotype relative to a control individual or the general population. Increased risk or increased predisposition may also be determined using other epidemiological methods such as for example calculation of a hazard ratio or a relative risk.

In addition to ICDs and CRT-Ds, VT, VF and SCA/SCD may also be suppressed or treated by the use of biologics such as gene therapy or pharmacological therapy. These pharmacological therapies can be referred to as anti-arrhythmic drugs (AADs) and are further sub-categorized based on the mechanism of action (e.g., Class I, Class II and Class III). In the first through thirteenth aspects of the invention, AADs can be used alone or in combination with ICDs or CRT-Ds. In particular, β-blocker and angiotensin converting enzyme (ACE) inhibitor therapies can be utilized in interrupting the mechanisms that lead progressively to a continuous impairment of myocardial function. Plasma norepinephrine levels are chronically elevated in patients with heart failure, with greater elevations correlating with a poor prognosis. The resulting increase in stimulation of the β-adrenergic system can lead to a desensitization of the adenylyl cyclase of the heart, which is due to a decrease in β-adrenoceptor density on the surface of the cardiac myocytes, an increased expression of the α-subunit of the inhibitory G-protein, and a phosphorylation of the adrenoceptors by increased activity and expression of the β-adrenoceptor kinase. The functional relevance of these cellular changes is reflected by a decreased response of the heart to catecholamines in vitro and in vivo. Furthermore, the chronic β-adrenergic activation causes an increase in heart rate, which leads to reduced myocardial blood flow due to a shortened coronary vascular diastolic perfusion time. The application of a β-blocker leads to a reduced heart rate, resulting in lower myocardial energy expenditure, prolonged diastolic filling and increased effective myocardial blood flow due to the prolonged coronary vascular diastolic perfusion time. Plasma norepinephrine levels are also reduced by β-blockers. In the first through thirteenth aspects of the invention, ICDs and CRT-Ds enhance the mortality-reducing effect of β-blockers, and can therefore be used together.

Methods for Detecting a SNP and Diagnostic/Therapeutic Uses

Genetic markers are non-invasive, cost-effective and conducive to mass screening of individuals. The SNPs identified herein can be effectively used alone or in combination with other SNPs as well as with one or more clinical and demographic markers and a patient's medical history for risk-stratification, assessment, and diagnosis susceptibility to SCA that can be treated with an anti-arrhythmic therapy, which may include pharmacological and/or device therapy (e.g., an ICD). The genetic markers taught herein provide greater specificity and sensitivity in identification of individuals that could benefit from receiving any one of a CRT CRT-D, or ICD to treat VA, SCA, SCD, or HF. In particular, the specific mutations of the present invention are directed to the specific purpose of identifying susceptibility to specific cardiac disease for patients requiring an ICD. The methods and compositions can be directed to specific mutations for the specific purpose of determining susceptibility to the particular diseases of Ventricular Arrhythmias (VA), Sudden Cardiac Arrest (SCA), Sudden Cardiac Death (SCD), or Heart Failure (HF).

To determine which versions of a SNP a person has, any embodiment of the first through thirteenth aspects of the invention contemplates: (1) collecting DNA from the test subject; (2) obtaining the DNA sequence of either the relevant genome section or the entire genome; and (3) analyzing the DNA sequence to determine which variant of a SNP is present. To obtain a DNA sample from a test subject, DNA can be analyzed from collected material, e.g. a cheek swab or blood sample. Sequencing DNA from the relevant genome section can involve a PCR reaction with primers that amplify a small portion of the genome (e.g., a few hundred to a few thousand base pairs) that incorporates the SNP to be tested. This PCR-amplified subsection of the genome can then be analyzed by a sequencing method that is commonly used to sequence relatively small DNA chains, such as Sanger sequencing or pyrosequencing. Alternatively, next-generation sequencing (NGS) techniques may be applied to the DNA sample, such as ion semiconductor sequencing or sequencing by synthesis. Next-generation sequencing is usually applied to large DNA samples and may include an entire human genome. Once a sequence is obtained, the relevant site of the SNP can be identified using the sequences listed in Table 1 as a reference and the identity of the SNP (e.g., C or T) can be determined.

In any embodiments of the first through thirteenth aspects of the invention, non-mutually exclusive methods of commercializing the testing of these SNPs on a scalable platform can be envisioned. In any embodiment of the first through thirteenth aspects of the invention, a "diagnostic kit" could be produced that contains the materials required to perform a PCR reaction and sequencing of a subsection of the genome. Such a diagnostic kit would consist mainly of relevant PCR primers, for the PCR reaction and for the sequencing reaction. The kit can also include components needed to isolate a DNA sample and/or buffers and enzymes to perform the PCR reaction.

In any embodiment of the first through thirteenth aspects of the invention, a software product could be developed that identifies the relevant SNPs in a digital DNA sequence (e.g. a fully sequenced genome), and reports on their status (e.g., C or T). In any embodiment of the first through thirteenth aspects of the invention, an NGS method can be used to obtain a DNA sequence. The DNA sequence can be uploaded into the software. The software can then scan the DNA sequence to locate the SNPs (using the sequences in Table 1), and can then determine which version of the SNP is present and display this result on a computer screen.

In any embodiment of the first through thirteenth aspects of the invention, test results can be accompanied by medical advice from an ICD. In particular, genetic variations can be associated with human phenotypic diversity and sometimes disease susceptibility. As such, variations in genes may prove useful as markers for disease or other disorders or conditions. Variation at a particular genomic location can be due to a mutation event in the conserved human genome sequence, leading to two or more possible nucleotide variants at that genetic locus. If both nucleotide variants are found in at least 1% of the population, that location can be defined as a Single Nucleotide Polymorphism ("SNP"). Moreover, SNPs in close proximity to one another can often be inherited together in blocks called "haplotypes."

One phenomenon of SNPs is linkage disequilibrium, which refers to the tendency of specific alleles at different genomic locations to occur together more frequently than would be expected by random change. Alleles at given loci are said to be in complete equilibrium if the frequency of any particular set of alleles (or haplotype) is the product of their individual population frequencies. Several statistical measures can be used to quantify this relationship. Devlin and Risch, *A comparison of linkage disequilibrium measures for fine-scale mapping*, GENOMICS, 1995 Sep. 20; 29(2):311-22.

Genetic markers can also be deleted parts of the genome, repeated parts of the genome, transposed parts of the genome, and single nucleotide polymorphisms (SNPs). DNA and RNA are related through transcription; RNA and proteins are related through translation; and proteins and disease are related through catalysis of reactions.

An allele found to have a higher than expected prevalence among individuals positive for a given outcome can be considered a "risk allele" for that outcome. An allele that is found to have a lower than expected prevalence among individuals positive for an outcome can be considered a "protective allele" for that outcome. While the human genome harbors 10 million "common" SNPs, minor alleles indicative of heart disease in some cases can only be shared by as little as one percent (1%) of a population.

As provided herein, certain SNPs found by one or a combination of these methods can be determined to be useful as genetic markers for risk-stratification of VA, SCD or SCA in individuals. Further, certain SNPs found by one or a combination of these methods can be useful as genetic markers for identifying subjects who are prone to VA, SCD, or SCA who would benefit from treatment using ICDs. Genome-wide association studies are used to identify disease susceptibility genes for common diseases and involve scanning thousands of samples, either as case-control cohorts or in family trios, utilizing hundreds of thousands of SNP markers located throughout the human genome. Algorithms can then be applied that compare the frequencies of single SNP alleles, genotypes, or multi-marker haplotypes between disease and control cohorts. Regions (loci) with statistically significant differences in allele or genotype frequencies between cases and controls, pointing to their role in disease, are then analyzed. For example, following the completion of a whole genome analysis of patient samples, SNPs for use as clinical markers can be identified by any, or a combination of, the following three methods:

(1) Statistical SNP Selection Method: Univariate or multivariate analysis of the data is carried out using Cox Regression to determine the correlation between the SNPs and the study outcome, potentially fast ventricular events (which may be associated with life-threatening ventricular events) for the first through thirteenth aspects of the invention. SNPs that yield low p-values are considered as markers. These techniques can be expanded by the use of other statistical methods such as linear regression.

(2) Logical SNP Selection Method: Clustering algorithms are used to segregate the SNP markers into categories which would ultimately correlate with the patient outcomes. Classification and Regression Tree ("CART") is one of the clustering algorithms that can be used. In that case, SNPs forming the branching nodes of the tree will be the markers of interest.

(3) Biological SNP Selection Method: SNP markers are chosen based on the biological effect of the SNP, as it might affect the function of various proteins. For example, a SNP located on a transcribed or a regulatory portion of a gene that is involved in ion channel formation would be a good candidate. Similarly, a group of SNPs that are shown to be located closely on the genome would also hint at the importance of the region and would constitute a set of markers.

An explanation of an rs number and the National Center for Biotechnology Information (NCBI) SNP database is provided herein. In collaboration with the National Human Genome Research Institute, The National Center for Biotechnology Information has established the Single Nucleotide Polymorphism Database (dbSNP) to serve as a central repository for both single base nucleotide substitutions, also known as single nucleotide polymorphisms (SNP) and short deletion and insertion polymorphisms. Reference Sequences, or RefSeqs (rs), are a curated, non-redundant set of records for mRNAs, proteins, contigs, and gene regions constructed from a GenBank exemplar for that protein or sequence. The rs numbers represent a unique record for a SNP. Submitted SNPs (ss) are records that are independently submitted to NCBI, are used to construct the rs record, and are cross-referenced with the rs record for the corresponding genome location. Submitter-Referenced Accession numbers are annotations that are included with a SS number. For rs records relevant to the first through thirteenth aspects of the invention, these accession numbers may be associated with a GenBank accession record, which will start with one or two letters, such as "AL" or "AC," followed by five or six numbers. The NCBI RefSeq database accession numbers have different formatting: "NT_123456." The RefSeq accession numbers are unique identifiers for a sequence, and when minor changes are made to a sequence, a new version number is assigned, such as "NT_123456.1," where the version is represented by the number after the decimal. The rs number represents a specific range of bases at a certain contig position. Although the contig location of the rs sequence may move relative to the length of the larger sequence encompassed by the accession number, that sequence of bases represented by the rs number, i.e., the SNP, will remain constant. Hence, it is understood that rs numbers can be used to uniquely identify a SNP and fully enables one of ordinary skill in the art to make and use the first through thirteenth aspects of the invention using rs numbers. The sequences provided in the Sequence Listing each correspond to a unique sequence represented by an rs number known at the time of invention. Thus, the SEQ ID NO.'s and the rs numbers disclosed herein are understood to represent uniquely identified sequences for identified SNPs and may be used interchangeably.

In any embodiment of the first through thirteenth aspects of the invention, the genotypes can be imputed at SNP locations where the genotype was not read using the haplotype data available from public databases and the actual SNP data obtained from the patients. This can be accomplished using the MACH haplotyper program (MACH 1.0, Gonçalo Abecasis and Yun Li), which takes advantage of a statistical technique known as Hidden Markov Model (HMM). MACH 1.0 is a Markov Chain based haplotyper that can resolve long haplotypes or infer missing genotypes in samples of unrelated individuals. MACH input files include information on experimental genotypes for a set of individuals and, optionally, on a set of known haplotypes. MACH can use estimated haplotypes for each sampled individual (conditional on the observed genotypes) or fill in missing genotypes (conditional on observed genotypes at flanking markers and on the observed genotypes at other individuals). The essential inputs for MACH are a set of observed genotypes for each individual being studied. Typically, MACH expects that all the markers being examined map to one chromosome and that appear in map order in the input files. These requirements can be relaxed when using phased haplotypes as input. MACH also expects observed genotype data to be stored in a set of matched pedigree and data files. The two files are intrinsically linked, the data file describes the contents of the pedigree file (every pedigree file is slightly different), and the pedigree file itself can only be decoded with its companion data file. The two files can use either the Merlin/QTDT or the LINKAGE format. Data files can describe a variety of fields, including disease status information, quantitative traits and covariates, and marker genotypes. A simple MACH data file simply lists names for a series of genetic markers. Each marker name appears in its own line prefaced by an "M" field code. The genotypes are stored in a pedigree file. The pedigree file encodes one individual per row. Each row should start with a family ID and individual ID, followed by a father and mother ID (which typically are both set to 0, "zero," since the current version of MACH assumes all sampled individuals are unrelated), and sex. These initial columns are followed by a series of marker genotypes, each with two alleles. Alleles can be coded as 1, 2, 3, 4 or A, C, G, T. For many analyses, but in particular for genotype imputation, it can be very helpful to provide a set of reference haplotypes as input. Reference haplotypes can include genotypes for markers that were not examined in the examined data set, e.g., GAME or MAPP, but that can frequently be imputed based on genotypes at flanking markers. Most commonly, these haplotypes are derived from a public resource such as the International HapMap Project and will be derived, eventually, from the 1000 Genomes Project.

In any embodiments, a non-transitory processor-readable medium can include code to cause a processor or special purpose computer to receive a set of genetic variants as described herein. The code can include code to cause the processor to identify the genetic variants, and the code further includes code to cause the processor to present the variants such that the subset of variants can be used to render a decision to implant an ICD.

Figure 2:
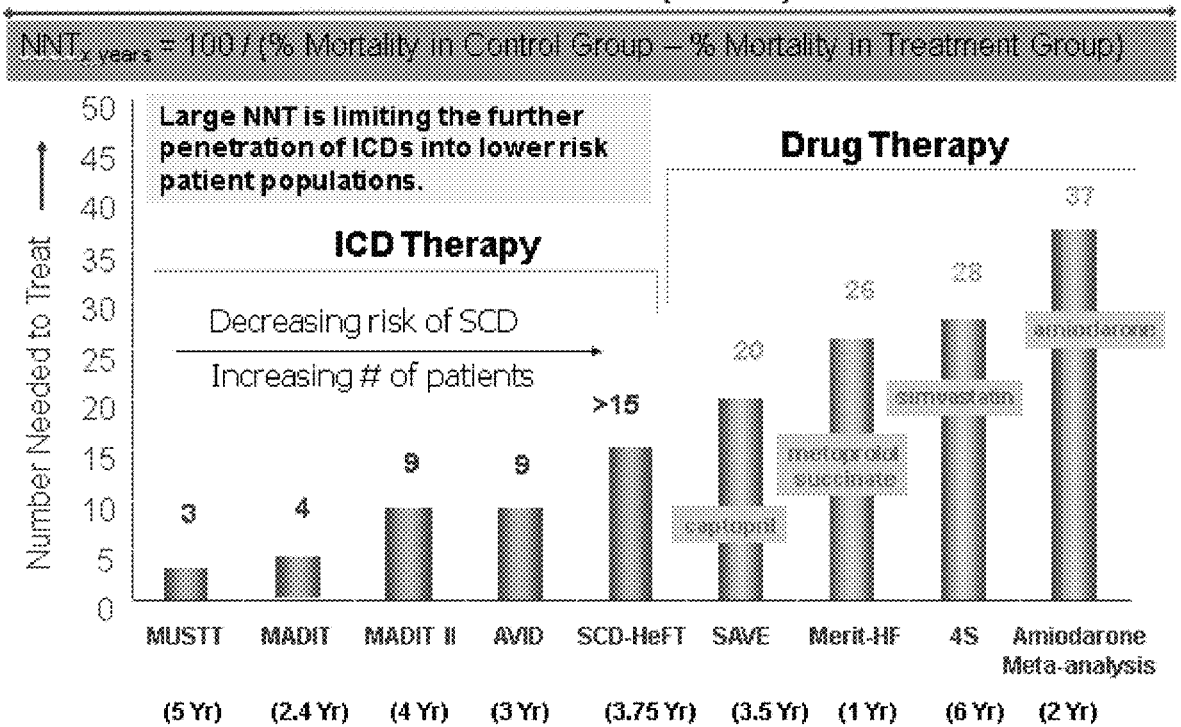
FIG. 2 is a bar graph depicting increase in the Number Needed to Treat ("NNT") observed for therapy as devices are implanted in patients with lower risks.

FIG. 2 shows an increase in the Number Needed to Treat ("NNT") can be been observed for ICD therapy as the devices are implanted in patients with lower risks. NNT is an epidemiological measure used in assessing the effectiveness of a health-care intervention. The NNT is the number of patients who need to be treated in order to prevent a single negative outcome. In the case of ICDs, currently, devices must be implanted in approximately 17 patients to prevent one death over approximately 4 years. The other 16 patients may not experience a life-threatening arrhythmia and may not receive a treatment over the specified duration of time. Reduction of the NNT for ICDs would yield to better patient identification methods and allow delivery of therapies to individuals who need them. As a result, it is believed that the need for risk stratification of patients might increase over time as the ICDs are implanted in patients who are generally considered to be at lower risk categories. The net result of the lack of more specific markers for life threatening arrhythmias is the presence of a population of patients who would benefit from ICD therapy, but are not currently indicated, and a subgroup of patients who receive ICD implants, but may not benefit from them.

DNA Microarrays and Kits

The first through thirteenth aspects of the invention provide methods for detecting a polynucleotide including at least a portion of the nucleotides represented by SEQ ID NO.'s 1-2. The portions are defined as nucleotide lengths sufficient to result in allele specific hybridization and to characterize the polymorphic site, either at position 26 or 27 in SEQ ID NO.'s 1-2 as defined herein. Preferably, the polynucleotide includes the entire genomic sequence represented by SEQ ID NO.'s 1-2. In one aspect, the method includes amplifying nucleotides complementary to SEQ ID NO.'s 1-2 of an individual to form amplified polynucleotides, and detecting the amplified polynucleotides. Preferably, nucleotides are amplified by PCR. In PCR, a molar excess of a primer pair is added to a biological sample that includes polynucleotides, preferably genomic DNA. The primers are extended to form complementary primer extension products which act as a template for synthesizing the desired amplified polynucleotides.

Figure 3:
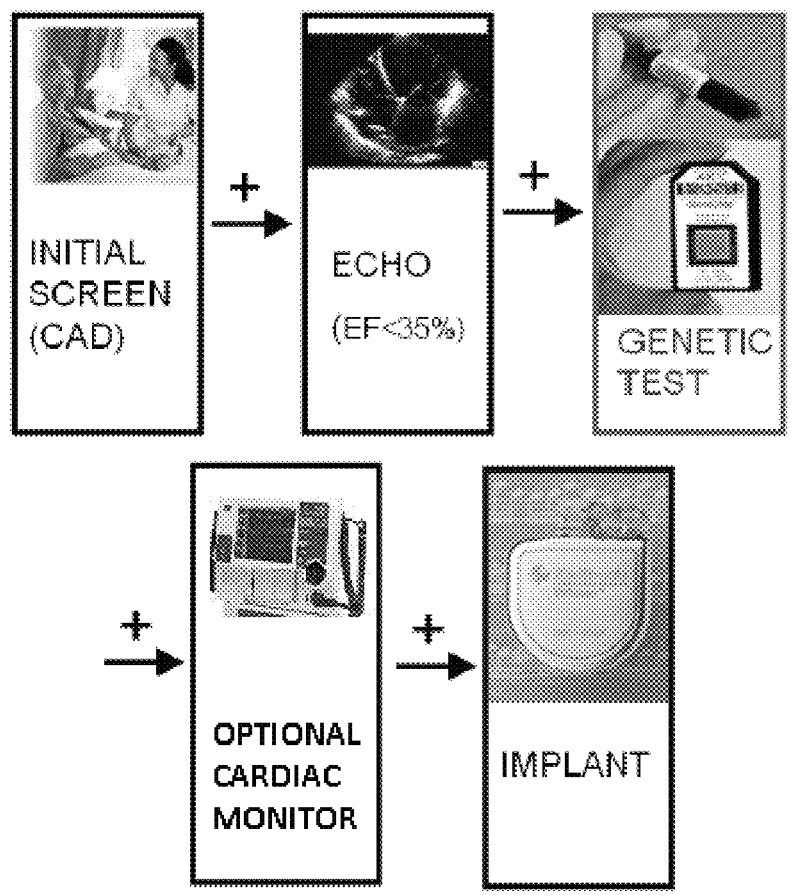
FIG. 3 is a flow chart of the operation of the genetic test in conjunction with existing medical tests.

FIG. 3 depicts one embodiment of the first through thirteenth aspects of the invention of a clinical utilization of the genetic test created for screening of patients for susceptibility to life threatening arrhythmias. In any embodiment of the first through thirteenth aspects of the invention, patients already testing positively for CAD and a low EF would undergo the test for genetic susceptibility using any of the methods described herein. Positive genetic test results would then be used in conjunction with the other test, such as the ones based on the analysis of ECG or cardiac monitors, and be used to make the ultimate decision of whether or not to implant an ICD.

Patients who are presenting a cardiac condition such as MI are usually subjected to echocardiographic examination to determine the need for an ICD. Based on the first through thirteenth aspects of the invention, blood samples could also be taken from the patients who have low left ventricular EF. If the genetic tests in combination with the hemodynamic and demographic parameters indicate a high risk for sudden cardiac arrest, then a recommendation is made for an ICD implant. A schematic of this overall process is shown in FIG. 3. A similar recommendation can be made for individuals with no previous history of cardiovascular disease based on a positive genetic screen for one or more of the SNPs taught herein in combination with one or more biological factors including markers, clinical parameters and/or like. In any embodiment of the first through thirteenth aspects of the invention, the genetic test can be used as follows: 1) administering the genetic test, 2) providing a clinical assessment, and then 3) placing the ICD in high risk individuals.

The methods that include amplifying nucleotides complementary to SEQ ID NO.'s 1-2 of an individual may be used to identify an individual not at risk for developing SCA. In this aspect, the primer pair includes primers that flank the polymorphism contained in the SEQ ID NO.'s 1-2. After amplification, the sizes of the amplified polynucleotides may be determined, for instance by gel electrophoresis, and compared. The amplified polynucleotides can be visualized by staining (e.g., with ethidium bromide) or labeling with a suitable label known to those skilled in the art, including radioactive and nonradioactive labels. Typical radioactive labels include $^{33}$P. Nonradioactive labels include, for example, ligands such as biotin or digoxigenin as well as enzymes such as phosphatase or peroxidases, or the various chemiluminescers such as luciferin, or fluorescent compounds like fluorescein and its derivatives.

Numerous forms of diagnostic kits employing arrays of nucleotides are known in the art. They can be fabricated by any number of known methods including photolithography, pipette, drop-touch, piezoelectric, spotting and electric procedures. The DNA microarrays generally have probes that are supported by a substrate so that a target sample is bound or hybridized with the probes. In use, the microarray surface is contacted with one or more target samples under conditions that promote specific, high-affinity binding of the target to one or more of the probes. A sample solution containing the target sample typically contains radioactively, chemoluminescently or fluorescently labeled molecules that are detectable. The hybridized targets and probes can also be detected by voltage, current, or electronic means known in the art.

Optionally, a plurality of microarrays may be formed on a larger array substrate. The substrate can be diced into a plurality of individual microarray dies in order to optimize use of the substrate. Possible substrate materials include siliceous compositions where a siliceous substrate is generally defined as any material largely comprised of silicon dioxide. Natural or synthetic assemblies can also be employed. The substrate can be hydrophobic or hydrophilic or capable of being rendered hydrophobic or hydrophilic and includes inorganic powders such as silica, magnesium sulfate, and alumina; natural polymeric materials, particularly cellulosic materials and materials derived from cellulose, such as fiber-containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. The surface of the substrate is then chemically prepared or derivatized to enable or facilitate the attachment or affixment of the molecular species to the surface of the array substrate. Surface derivatizations can differ for immobilization of prepared biological material, such as cDNA, and in situ synthesis of the biological material on the microarray substrate. Surface treatment or derivatization techniques are well known in the art. The surface of the substrate can have any number of shapes, such as strip, plate, disk, rod, particle, including bead, and the like. In modifying siliceous or metal oxide surfaces, one technique that has been used is derivatization with bifunctional silanes, i.e., silanes having a first functional group enabling covalent binding to the surface and a second functional group that can impart the desired chemical and/or physical modifications to the surface to covalently or non-covalently attach ligands and/or the polymers or monomers for the biological probe array. Adsorbed polymer surfaces are used on siliceous substrates for attaching nucleic acids, for example cDNA, to the substrate surface. Since a microarray die may be quite small and difficult to handle for processing, an individual microarray die can also be packaged for further handling and processing. For example, the microarray may be processed by subjecting the microarray to a hybridization assay while retained in a package.

Various techniques can be employed for affixing an oligonucleotide for use in a microarray. In situ synthesis of oligonucleotide or polynucleotide probes on a substrate is performed in accordance with well-known chemical processes, such as sequential addition of nucleotide phosphoramidites to surface-linked hydroxyl groups. Indirect synthesis may also be performed in accordance with biosynthetic techniques such as Polymerase Chain Reaction ("PCR"). Other methods of oligonucleotide synthesis include phosphotriester and phosphodiester methods and synthesis on a support, as well as phosphoramidate techniques. Chemical synthesis via a photolithographic method of spatially addressable arrays of oligonucleotides bound to a substrate made of glass can also be employed. The affixed probes or oligonucleotides, themselves, can be obtained by biological synthesis or by chemical synthesis. Chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers.

Immobilization of probes or oligonucleotides on a substrate or surface may be accomplished by well-known techniques. One type of technology makes use of a bead-array of randomly or non-randomly arranged beads. A specific oligonucleotide or probe sequence is assigned to each bead type, which is replicated any number of times on an array. A series of decoding hybridizations is then used to identify each bead on the array. The concept of these assays is very similar to that of DNA chip-based assays. However, oligonucleotides are attached to small microspheres rather than to a fixed surface of DNA chips. Bead-based systems can be combined with most of the allele-discrimination chemistry used in DNA chip-based array assays, such as single-base extension and oligonucleotide ligation assays. The bead-based format has flexibility for multiplexing and SNP combination. In bead-based assays, the identity of each bead is determined where that information is combined with the genotype signal from the bead to assign a "genotype call" to each SNP and individual.

One bead-based genotyping technology uses fluorescently coded microspheres developed by Luminex. Fulton R., et al, *Advanced multiplexed analysis with the FlowMetrix system,* CLIN. CHEM., 1997; 43: 1749-56. These beads are coated with two different dyes (red and orange), and can be identified and separated using flow cytometry, based on the amount of these two dyes on the surface. By having a hundred types of microspheres with a different red:orange signal ratio, a hundred-plex detection reaction can be performed in a single tube. After the reaction, these microspheres are distinguished using a flow fluorimeter where a genotyping signal (green) from each group of microspheres is measured separately. This bead-based platform is useful in allele-specific hybridization, single-base extension, allele-specific primer extension, and oligonucleotide ligation assay. In a different bead-based platform commercialized by Illumina, microspheres are captured in solid wells created from optical fibers. Michael K. et al., *Randomly ordered addressable high-density optical sensor arrays,* ANAL. CHEM., 1998; 70: 1242-48; Steemers F. et al., *Screening unlabeled DNA targets with randomly ordered fiber-optic gene arrays,* NAT. BIOTECHNOL., 2000; 18: 91-94. The diameter of each well is similar to that of the spheres, allowing only a single sphere to fit in one well. Once the microspheres are set in these wells, all of the spheres can be treated like a high-density microarray. The high degree of replication in DNA microarray technology makes robust measurements for each bead type possible. Bead-array technology is particularly useful in SNP genotyping. Software used to process raw data from a DNA microarray or chip is well known in the art and employs various known methods for image processing, background correction and normalization. Many available public and proprietary software packages are available for such processing whereby a quality assessment of the raw data can be carried out, and the data then summarized and stored in a format which can be used by other software to perform additional analyses.

Hybridization probes can be labeled with a radioactive substance for easy detection. Grunstein et al. (PROC. NATL. ACAD. SCI. USA, 1975; 72:3961) and Southern (J. MOL. BIOL., 1975; 98:503) describe hybridization techniques using radio-labeled nucleic acid probes. Advantageously, nucleic acid hybridization probes can have high sensitivity and specificity. Radioactive labels can be detected with a phosphor imager or autoradiography film. Radioactive labels are most often used with nylon membrane macro-arrays. Suitable radioactive labels can be, for example, but not limited to isotopes like $^{125}$I or $^{32}$P. The detection of radioactive labels is, for example, performed by the placement of medical X-ray film directly against the substrate which develops as it is exposed to the label, which creates dark regions which correspond to the emplacement of the probes of interest.

Known methods of electrically detecting hybridization can be used such as electrochemical impedance spectroscopy. This technique can be used to investigate the changes in interfacial electrical properties that arise when DNA-modified Si(1 1 1) surfaces are exposed to solution-phase DNA oligonucleotides with complementary and non-complementary sequences. The n- and p-type silicon (1 1 1) samples can be covalently linked to DNA molecules via direct Si—C linkages without any intervening oxide layer. Exposure to solutions containing DNA oligonucleotides with the complementary sequence can produce significant changes in both the real and imaginary components of electrical impedance, while exposure to DNA with non-complementary sequences generate negligible responses. These changes in electrical properties can be corroborated with fluorescence measurements and reproduced in multiple hybridization-denaturation cycles. Additionally, the ability to detect DNA hybridization is strongly frequency-dependent wherein modeling of the response and comparison of results on different silicon bulk doping shows that the sensitivity to DNA hybridization arises from DNA-induced changes in the resistance of the silicon substrate and the resistance of the molecular layers. Wei et al., *Direct electrical detection of hybridization at DNA-modified silicon surfaces*, BIOSENSORS AND BIOELECTRONICS, 2004 Apr. 15; 19(9): 1013-9. In addition, macroporous silicon can be used as an electrical sensor for real time, label free detection of DNA hybridization whereby electrical contact is made exclusively on a back side of a substrate to allow complete exposure of a porous layer to DNA. Hybridization of a DNA probe with its complementary sequence produces a reduction in the impedance and a shift in the phase angle resulting from a change in dielectric constant inside the porous matrix and a modification of a depletion layer width in the crystalline silicon structure. Again, the effect of the DNA charge on the response can be corroborated using peptide nucleic acid (PNA), which is an uncharged analog of DNA.

Sudden Cardiac Arrest (SCA)

Sudden Cardiac Arrest (SCA), also known as Sudden Cardiac Death (SCD), results from an abrupt loss of heart function. It is commonly brought on by an abnormal heart rhythm. SCD occurs within a short time period, which is generally less than an hour from the onset of symptoms. Despite recent progress in the management of cardiovascular disorders generally, and cardiac arrhythmias in particular, SCA remains a problem for the practicing clinician as well as a major public health issue.

In the United States, SCA accounts for the loss of over 300,000 individuals each year. More deaths per annum are attributable to SCA than to lung cancer, breast cancer, or AIDS. This represents an incidence of 0.1-0.2% per year in the adult population. Myerburg, R J et al., *Cardiac arrest and sudden cardiac death*, Braunwald E, ed., *A TEXTBOOK OF CARDIOVASCULAR MEDICINE*. $6^{TH}$ ED., Philadelphia, Saunders, W B., 2001; 890-931; *American Cancer Society, Cancer Facts and FIG.'s* 2003; 4; *Center for Disease Control* 2004.

In approximately 80% of cases, SCA occurs in the setting of Coronary Artery Disease ("CAD"). Most instances involve Ventricular Tachycardia ("VT") degenerating to Ventricular Fibrillation ("VF") and subsequent asystole. Fibrillation occurs when transient neural triggers impinge upon an unstable heart causing normally organized electrical activity in the heart to become disorganized and chaotic. Complete cardiac dysfunction results. Non-ischemic cardiomyopathy and infiltrative, inflammatory, and acquired valvular diseases account for most other SCA, or SCD, events. A small percentage of sudden cardiac arrest events occur in the setting of ion channel mutations responsible for inherited abnormalities such as the long/short QT syndromes, Brugada syndrome, and catecholaminergic ventricular tachycardia. These conditions account for a small number of events. In addition, other genetic abnormalities such as hypertrophic cardiomyopathy and congenital heart defects such as anomalous coronary arteries may contribute to an increased risk for SCA.

Association of genetic variation and disease can be a function of many factors, including, but not limited to, the frequency of the risk allele or genotype, the relative risk conferred by the disease-associated allele or genotype, the correlation between the genotyped marker and the risk allele, sample size, disease prevalence, and genetic heterogeneity of the sample population. In order to search for associations between SNPs and patient outcomes, genomic DNA can be isolated from the blood samples collected from patients. Following DNA isolation, a whole genome scan can be conducted using gene chips known to those skilled in the art, (e.g., Illumina 1MM HapMap gene chips). For each locus, two nucleic acid reads can be performed for each patient, representing the nucleotide variants on two chromosomes, except for the loci chromosomes on male patients. Following compilation of the genetic data into an electronic database, statistical analysis can be carried out.

ICDs are implanted in approximately 250,000 individuals in the United States each year for criteria that include diminished ejection fraction (EF), symptomatic heart failure, and, to a lesser extent, prolongation of the QRS interval or other electrophysiologic markers such as microvolt T-wave alternans or late potential on signal-averaged electrocardiograms. Although ICDs have a success rate of more than 97% for sensing and terminating life threatening arrhythmias, only approximately 25% of patients receiving an ICD require treatment for a life-threatening arrhythmia over a 4-year period after implantation. Accordingly, the current criteria for selecting patients are rather crude, particularly when one considers that the ICDs are associated with various complications, including infection, lead failures, device malfunctions, and inappropriate shocks.

GNAS Proteins and Biomarkers

Common genetic variations can modify the susceptibility of individuals to certain diseases. Thus, genetic factors can also modulate the risk of arrhythmias and SCA, and identification of common variants could help to identify patients who are at risk. As described herein, potential genetic markers for SCA can be located in a gene coding the G-protein. The G-protein is composed of the three subunits ($\alpha$, $\beta$ and $\gamma$) and can interact with heptahelical transmembrane receptors, such as adrenoceptors, in intracellular signaling cascades relevant to various physiological functions, including those of the cardiovascular system. Thus, the G-protein can be involved in signal transduction of receptors involved in the regulation of ventricular rhythm. Moreover, some evidence has indicated that the G-protein might be directly involved in the genesis of atrial and ventricular arrhythmias.

In particular, the GNB3 gene consists of 12 exons localized on chromosomal position 12p13. The GNB3 SNP is rs5443, which codes for the $\beta_3$ subunit of the heterotrimeric G-proteins. The widely distributed c.825C>T polymorphism of this gene exhibits an exchange between Cytosine (C) and Thymine (T) in nucleotide position 825 of the cDNA. As G-proteins participate in signal transduction in almost all body cells, it was shown that this polymorphism is correlated with arterial hypertension, arteriosclerosis, and obesity, along with changes in the response to hormones and drugs. Homozygotes of the 825T-allele exhibit changes in ion current in atrial cells and results in reduced risk of atrial fibrillation. Additionally, the results of a recent retrospective pilot study suggest that the c.825C>T polymorphism of the GNB3 gene may have a modifying effect on the propensity towards life-threatening arrhythmias in patients with an ICD.

Polymorphisms occurring in the GNB3 gene are associated with changes in cellular signal transduction, and are correlated with arterial hypertension, arteriosclerosis and obesity. VT/VF are more prevalent in CC-homozygotes than in TC-heterozygotes and TT-homozygotes.

The GNAS gene codes for the Gαs-subunit of heterotrimeric G-proteins. Activation of Gαs (formerly the stimulating G-protein) activates adenyl cyclase, leading to increases in cAMP levels. Gαs is activated by many hormone receptors. The activation of $β_1$-adenoreceptors is particularly important for the heart, as this leads to positive chronotropy and inotropy. Several somatic mutations in GNAS lead to rare endocrinological diseases. There is also a silent c.393C>T-polymorphism thought to influence the response to β-blockers. A series of polymorphisms in the promoter and intron-1 of gene GNAS has recently been described; these modify the transcription rate and protein expression (c.-1211G>A, c.2291T>C).

Polymorphisms occurring in the GNAS gene are associated with codes from the Gαs-subunit of hetero-trimeric G-proteins. Activation of Gαs activates adenyl cyclase, leads to increases in cAMP. Gαs is activated by many hormone receptors. Activation of β1-adenoceptors can be particularly important for the heart, and may lead to positive chronotropy and inotropy.

The gene GNAQ codes for the G αq-protein transmits signals over $α_1$-adrenoreceptors (nor-adrenaline), endothelin receptors, as well as some other receptors. Gαq directly regulates many ion channels. Over-expression of Gαq in the heart leads to cardiac hypertrophy, whereas the knockout of Gαq (plus Gα11) counteracts the pressure-induced hypertrophy. Three new polymorphisms have recently been described in the promoter of gene GNAQ; these cause alterations in the expression of the Gαq protein—c.-909/-908GC>TT, c.-382G>A, and c.-387G>A.

Polymorphisms occurring in the GNAQ gene code for the Gαq-subunit of hetero-trimeric G-proteins. The Gαq-protein transmits signals over α1-adrenoreceptors (nor-adrenaline), endothelin receptors and similar receptors. Gαq directly regulates many ion channels. Hyper expression of Gαq in the heart leads to cardiac hypertrophy.

A detailed description is provided herein for Single Nucleotide Polymorphisms (SNPs) found on the G proteins, specifically of the "s pathway" G protein GNAS. Such G proteins are activated through a receptor that receives an extracellular signal. The relevant G protein-coupled receptor is the β1 adrenergic receptor, which is mostly expressed in cardiac tissue. As described herein, the β1 receptor is one of three β adrenergic receptors that are activated by epinephrine and closely related norepinephrine. (Nor)epinephrine is also called (nor)adrenaline, and is a human hormone and neurotransmitter. Epinephrine via the β1 receptor activates GNAS and the downstream cascade with a number of effects that include an increase of the heart rate (chronotropic effect), an increase of the contractility of the heart muscle (inotropic effect), and an increase of the electrical conductivity in the heart's atrioventricular (AV) node (dromotropic effect). These three effects contribute to increased cardiac output. Exogenous compounds (i.e., chemical compounds that are administered to the body, e.g. via intravenous injection, rather than produced by the body itself) may also activate or inhibit the β1 adrenergic receptor. Such compounds are called agonists or antagonists. An example of a β adrenergic agonist is isoprenaline (trade name Medihaler-Iso or Isuprel). Antagonists of β adrenergic receptor are known as beta blockers, examples of which are Acebutolol (Sectral/Prent), Bisoprolol (Concor) and Metoprolol (Lopressor). Agonists function as cardiac stimulants, for example to treat bradycardia (slow heart rate), while antagonists weaken the effects of epinephrine and are used to manage arrhythmias, protect from additional heart attacks, and treat hypertension.

Discovery Methodology

The purpose of DISCOVERY was to determine whether any of seven single nucleotide polymorphisms (SNP) in three genes coding for G-protein subunits were predictive of ventricular tachyarrhythmias (VT) in patients with implantable cardioverter defibrillators (ICD) without a prior history of VT. The study sought to determine whether genetic polymorphisms can identify patients at risk of VT with Primary Prevention ICD. Polymorphisms associated with ventricular tachyarrhythmias were determined using endpoints of the "diagnostic data influence on disease management and relation of genomics to ventricular tachyarrhythmias in implantable cardioverter/defibrillator patients" ("DISCOVERY") study (Wieneke et al., 12 EUROPACE, European Society of Cardiology, 2010, p. 424-429, the contents of which are incorporated by reference in their entirety. In particular, the DISCOVERY study design consisted of an interventional study, with ICD implantation for all enrolled patients, blood sampling, programming requirements and follow-up windows; "European" multi-center, non-randomized, prospective; a sample size of 1,223 patients enrolled at 91 centers in twelve countries across Europe. Electronic device interrogation files, with all detected tachyarrhythmia events, were collected at baseline and at all follow-up visits. All detected arrhythmias that met the qualifying primary endpoint definition were adjudicated by a panel of individuals with expertise in arrhythmia classification. The individuals adjudicating the arrhythmias were blinded to the genetic information. Blood samples were taken to assess genotype in 7 SNPs in 3 genes coding for G-protein subunits—C825T in GNB3, GC(909/908)TT, G(382)A and G(387)A in GNAQ and C393T, C2273T and T2291C in GNAS. Arrhythmia data were collected directly from the devices from the time of implant. The median follow-up time was 575 days with an interquartile range of 364-730 days. Univariate and multivariate Cox Regression were used to determine the predictive strength of the genetic and selected non-genetic variables in predicting time to first sustained VT (≥18 beats, ≥150 bpm). Because VT/VF episodes were treated by implanted devices, it is not possible to fully understand whether the episodes would have been lethal without treatment. As an alternative to determining whether episodes would have been lethal, the episodes were classified by their cycle length into three zones. Slow zone arrhythmias were defined as VT cycle lengths of >300 and ≤400 ms, Medium zone arrhythmias were defined as VT cycle lengths of >240 and ≤300 ms, and Fast zone arrhythmias were defined VT cycle lengths of ≤240 ms. Separate time to event analyses were done for episodes that fell into each of the three zones. There were 242 patients with at least one episode in the Slow zone, 100 patients with at least one episode in the Medium zone, and 52 patients with at least one episode in the Fast zone.

There were 1145 patients genotyped and with VT episodes adjudicated, with a mean age of 62, 963 males (84%), 638 subjects with a history of ischemic and 373 with a history of non-ischemic cardiomyopathy. Allele frequencies in the cohort were 51% T for C393T and 37% T for C2273T and were both in Hardy-Weinberg equilibrium.

As part of the study, candidate gene polymorphisms involved in coding of the G-protein subunits were correlated with the occurrence of ventricular arrhythmias in patients receiving an ICD for primary prevention. Additionally, a genome-wide association study was conducted to seek associations of SNPs with ventricular arrhythmias. The primary endpoint of the study is defined as the occurrence of a sustained ventricular arrhythmia with a maximal cycle length of 400 ms, at a bpm >150. This was chosen to include the majority of true arrhythmias while rejecting most of the false detections.

All enrolled patients received a single- or dual-chamber ICD with Cardiac Compass™ for recording long-term clinical trends. There were 13 patients that had device changes during the course of the study. Most of these changes did not result in a change of the single/dual chamber status and the ones that did either did not have a VT event nor had a VT event prior to the device change.

Inclusion criteria included: first implantation of a market approved Medtronic single- or dual-chamber ICD with long-term clinical trends; subjects requiring the implantation of an ICD for primary prevention according to the current AHA/ACC/ESC guidelines; subject is willing and able to comply with the Clinical Investigation Plan; subject is expected to remain available for follow-up visits; subject has signed the informed consent form within 10 days of implant; and the system implanted for this study is the first ICD implant for the patient.

Figure 4:
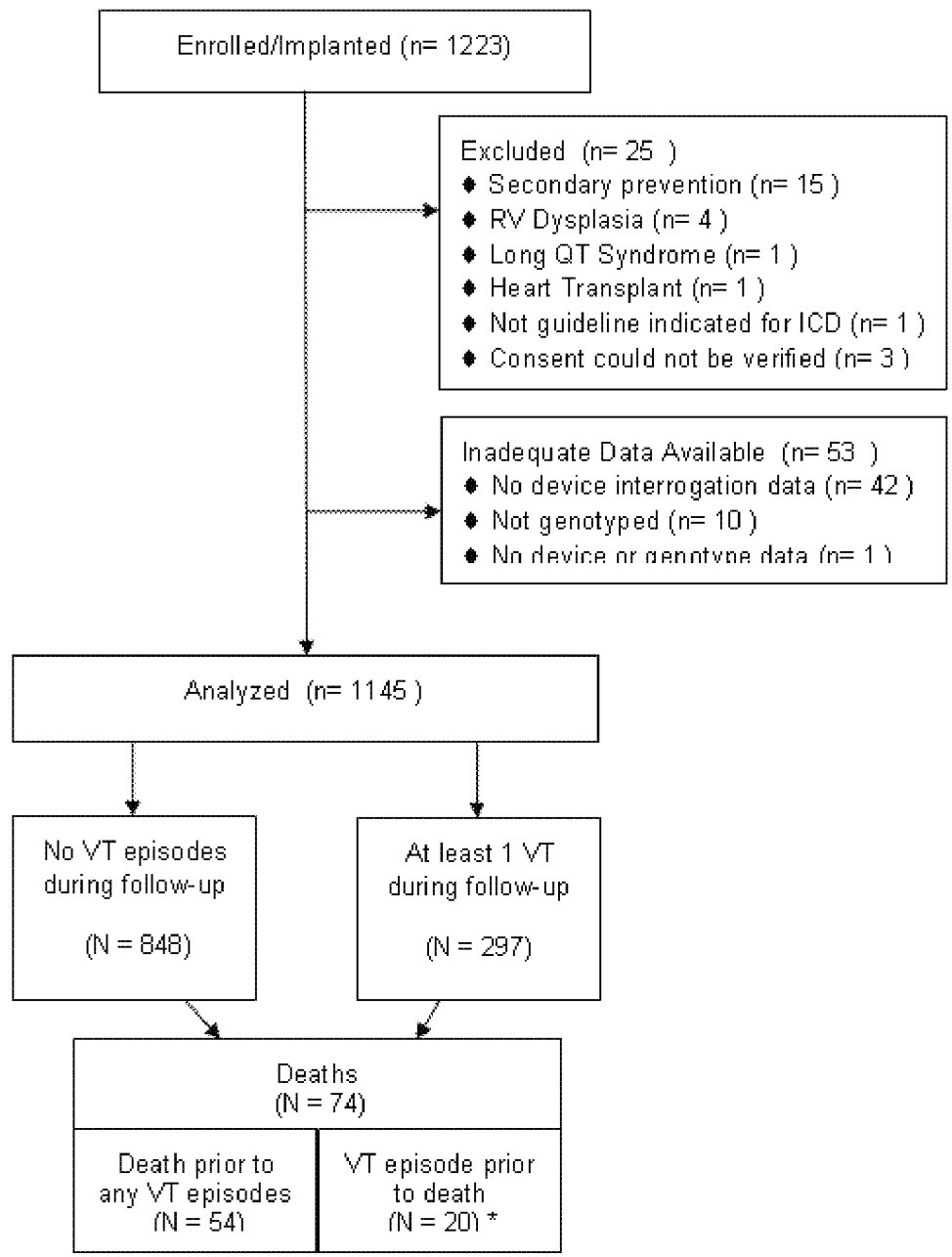
FIG. 4 is a CONSORT diagram for the DISCOVERY study, indicating details of patient flow within the study execution.

Exclusion criteria included: women who are pregnant, or women of childbearing potential who are not on a reliable form of birth control; subjects enrolled in a concurrent study that may confound the results of this study; subjects <18 years of age, or subjects under a minimum age that is required as defined by local law; subjects with life expectancy <2 years; subjects that had post-heart transplant or awaiting heart transplantation; subjects anticipated to demonstrate poor compliance; and subjects with syndromes known to be associated with ion channel pathologies, such as long- or short-QT syndrome, Brugada syndrome, Catecholaminergic polymorphic ventricular tachycardia (CPTV). The enrollment and exclusion of patients in the study is shown in FIG. 4. 25 patients had to be excluded from the study as they did meet an exclusion criterion and 53 patients had to be excluded from the final analysis as data sets were incomplete.

Patients were followed for a mean time period of 575 days with an interquartile range of 364-730, with clinical visits at 6, 12, 18 and 24 months following the ICD implantation. During each follow-up, the device was interrogated and all the data stored for later analysis. A blinded episode-reviewing committee reviewed and classified all reported spontaneous arrhythmias recorded by the devices during the study. The review of each episode was performed independently by at least two experienced cardiologists. Blood samples were collected from each patient during the initial implant procedure. A 20 mL sample of blood was collected and shipped directly to the core laboratory in Germany. Genotyping of the candidate gene polymorphisms was performed at the end of the study according to modified polymerase chain reaction-based methods. Samples were initially analyzed for seven SNPs in the genes GNB3, GNAQ, and GNAS. For the analysis of the predictive power of the various SNPs sensitivity, specificity and positive and negative predictive values were calculated as predictors of ventricular arrhythmia ≥400 ms.

The sample size is determined based on the accuracy requirements for the positive predictive value (PPV) of the desired risk stratification test. A 95% confidence interval with a maximal width of +/−5% was deemed appropriate for the accuracy of the PPV. Assuming that the actual PPV is 40%, a sample size of 386 patients is needed to reach this level of accuracy. Here, the bisection method is used along with the proportion confidence interval formulas as described by Johnson and Kotz. DISCOVERY is sufficiently powered to evaluate markers expressed in more than one-third of all patients. Since 386 patients with arrhythmias are needed to reach the primary endpoint, at least 3×386=1158 patients with a primary indication for ICD implantation were enrolled.

The secondary objectives of the study were to evaluate PPV of SNPS in the genes GNB3, GNAS and GNAQ as a predictor for death, cardiac death and atrial arrhythmia, and other SNPs involving signal transduction components which impact on the activity of cardiac ion channels. Another secondary object was to evaluate PPV for best combination of genetic markers, baseline and FU data as a predictor of PE, death, cardiac death and atrial arrhythmia. Additional secondary objectives included evaluating the frequency of programming changes involving AF-prevention and AF-therapy algorithms; evaluate the usage of ICD-system diagnostics, such as batter status, impedance, pacing threshold and sensing resulting in medical consequences; evaluate the use of ICD-based patient diagnostic, including arrhythmia, IEGM, heart frequency, % pacing and Cardiac Compass, resulting in medical consequences; and evaluate the frequency of pacing-parameter programming changes and the resulting medical consequences.

The secondary endpoints of the study were death/all-cause mortality based on information on Death CRF, and cardiac death based on death classification on Death CFR, as adjudicated by an Adverse Event Adjudication Committee (AEAC). Additional secondary endpoints include an atrial arrhythmia as document by ICD using an SVT or AT/AF episode log, and based on investigator classification of device episode in FU CRF III and adjudicated by two blinded independent physician reviewers using cardiac compass data. Additional secondary endpoints included programming changes of AF-prevention and AF-therapy algorithms, and medical consequences including hospitalization, medical interventions, medication, surgery and ICD-programming changes.

The baseline for the study comprised patient screening against DISCOVERY eligibility criteria; informing the patient and obtaining properly signed and dated consent forms; recording patient demographics, medical history, cardiovascular status and history, arrhythmia history, physical assessment (including LV ejection fraction, 12-lead ECG), NYHA class, and cardiovascular medications; and blood testing for the genomics analyses.

The baseline blood test was collected during hospitalization prior to the ICD implant. Kits were then provided to the core laboratory.

With regard to the implant, the surgical procedure for ICD implantation was at the discretion of the physician. Ventricular defibrillation testing was recommended at a 10J safety margin; however, the investigator was free to use his or her preferred method. Final device programming was stored on a save-to-disk file, and occurred one or more day(s) post-implant, but prior to discharging the patient as shown in Table 1 below.

TABLE 1

| Visits | Days post Device-Implantation | | |
|---|---|---|---|
| | Window start | Target day | Window end |
| 6-month follow-up | 153 | 183 | 213 |
| 12-month follow-up | 335 | 365 | 395 |
| 18-month follow-up | 518 | 548 | 578 |
| 24-month follow-up | 700 | 730 | 760 |

The follow-up included FU duration, symptoms, hospitalizations, cardioversions, save-to-disk files and classification of arrhythmias. For medical decisions taken during the FU visit, the use of diagnostics was explored with regard to device related diagnostics, such as battery status, sensing, pacing threshold and impedance, and patient related diagnostics such as arrhythmia/IEGM, heart frequency, % pacing and cardiac compass.

Adverse event reporting included Serious Adverse Device Effect (SADE), an ADE that has resulted in any of the consequences characteristic of an SAE or that might have led to any of these consequences if suitable action had not been taken or intervention had not been made or if circumstances had been less opportune. Additionally, Serious Procedure-Related AE is an SAE that occurs due to any procedure specific to the clinical investigation, including the implantation or modification of the system. A Serious Adverse Event (SAE) is described as an adverse event that led to death; led to a serious deterioration in the health of a subject that: resulted in a life-threatening illness or injury, resulted in a permanent impairment of a body structure or a body function, required in-patient hospitalization or prolongation of existing hospitalization, or resulted in medical or surgical intervention to prevent permanent impairment to body structure or a body function; or led to fetal distress, fetal death or a congenital abnormality or birth defect. Detected ventricular or supra-ventricular arrhythmias should not be considered adverse events, whether or not treated, as they constituted the objective of the study and are reported as study endpoints.

Patients were withdrawn from the study on the grounds of missing two consecutive follow-up visits, routinely failing to complete required procedures, lost to follow up, or no longer compliant with the in/exclusion criteria.

Discovery Primary Endpoint Multivariate Analysis

Figure 5:
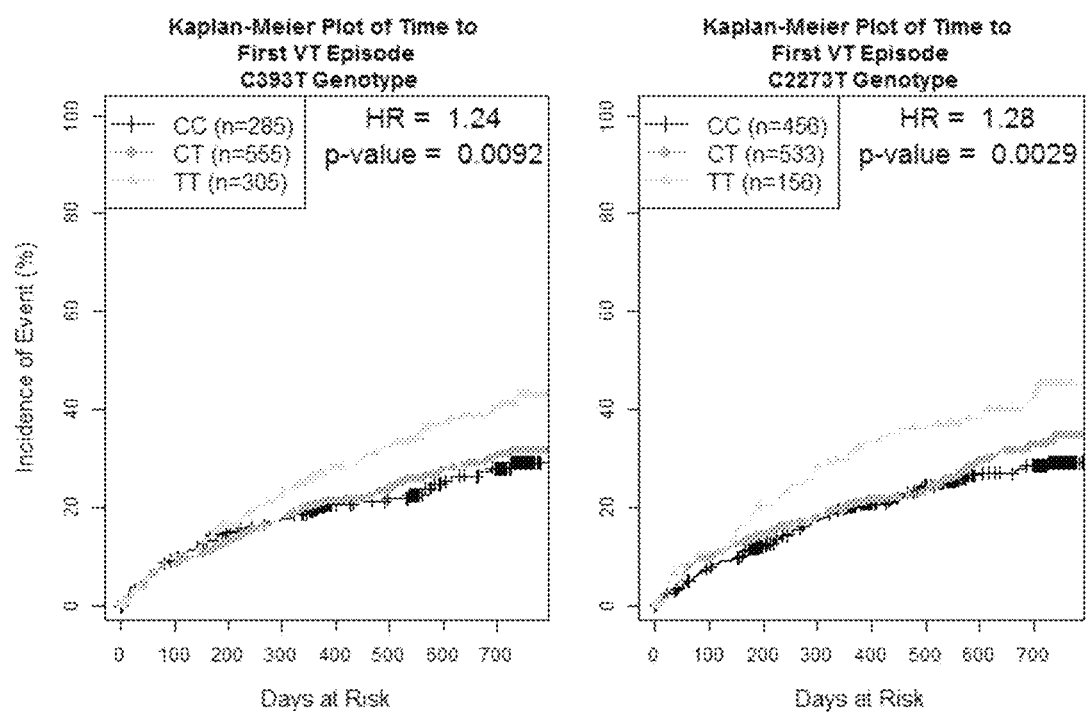
FIG. 5 is a plot showing the univariate results of the DISCOVERY study for GNAS c393 C>T and GNAS c2273 C>T as incidence of event over time to first fast VT or last visit.

Seven SNPs in 3 genes coding for G-protein subunits—C825T in GNB3, GC(-909/-908)TT, G(-382)A and G(-387)A in GNAQ and C393T, C2273T and T2291C in GNAS were studied in the Discovery study. Of all the SNPs in the DISCOVERY study, none of the 7 observed genotype distributions deviated from Hardy-Weinberg equilibrium and all had prevalence measures that matched those reported for Caucasian populations. Two SNPs in the GNAS gene, C393T and C2273T, were significant univariate predictors of VT incidence. Kaplan Meier plots of the time to first VT episode for patients with each genotype are shown in FIG. 5.

Both SNPs remained significant (HR=1.3, Likelihood Ratio p=0.046 for C393T and HR=1.4, Likelihood Ratio p=0.027 for C2273T) in a multivariate model, including history of non-sustained VT, left ventricular ejection fraction, QRS duration, gender and history of non-ischemic cardiomyopathy. In a permutation-based method to control for family-wise error rate over the 7 comparisons, C2273T remained significant and C393T bordered on significance (p<0.1). Within the analysis population, the 2 significant GNAS SNPs were moderately linked (correlation=-0.277; D'=0.369) and are located 9752 nucleotides from each other.

A retrospective subgroup analysis indicated that in the subgroup of patients with a history of ischemic cardiomyopathy, only the C393T TT genotype remained as a significant predictor of VT (HR=2.1, p<0.0052), while in subjects with a history of non-ischemic cardiomyopathy, only the C2273T TT genotype remained a significant predictor of VT (HR=1.76, p=0.0006).

Without being limited to any particular theory, it is believed that while subjects with ischemic disease have a lower incidence of VT episodes than subjects with nonischemic disease within the DISCOVERY study, ischemic patients with the TT genotype for C393T have an increased VT risk to the point that they have similar VT risk to nonischemic patients. In the nonischemic patients, there does not appear to be a C393T genotype effect. Regardless of cardiomyopathy etiology, there is an increased VT risk with the C2273T genotype.

The GNAS SNPs described herein (e.g., SEQ ID No.'s 1 and 2) can affect the expression level of the GNAS protein, which in turn can affect the efficacy of cardiac resynchronization therapy (CRT), generally. Because CRT operates on top of β-blockers, and because patients who are not on optimal β-blocker therapy have a higher risk of CRT non-response, without being limited to any particular theory, mutations in GNAS, which impair β-blocker response, may also influence CRT response. As such, in any embodiment of the first through thirteenth aspects of the invention, the SNPs as described herein may be predictors of the efficacy of CRT and/or ICD therapy. The DISCOVERY study shows a genetic risk stratifier, independent of other clinical risk factors, and for the first time introduces a new G-protein mediated mechanism of arrhythmia. The primary study objective was to explore whether any of 7 SNPs in 3 genes coding for G-protein subunits are predictive of time to arrhythmia.

Because DISCOVERY was a prospective study of subjects who were guideline indicated for and received an initial implant of an ICD, subjects were followed for 24 months after implant and blood samples were used to assess genotype in 7 SNPs in 3 genes coding for G-protein subunits—C825T in GNB3, GC(-909/-908)TT, G(-382)A and G(-387)A in GNAQ and C393T, C2273T and T2291C in GNAS. All spontaneous ventricular tachycardia (VT) episodes since ICD implant were saved in the device and adjudicated by an independent, blinded board, including at least two physicians. Univariate analysis was performed on the results of the two-year follow-up, with a Cox regression performed for each SNP, modeled as ordinal variables with values set to the number of minor alleles. A hazard ratio and Bonferroni-adjusted p-values are calculated for each SNP. In particular, univariate and multivariate Cox Regression was used to determine the predictive strength of time to first adjudicated VT (<400 msec, >150 bpm).

The results of the study show that C2273T (rs12481583) can be a significant univariate predictor of time to ventricular tachycardia (VT) and that C393T (rs7121) was close enough to merit additional study (Bonferroni-adjusted p-value=0.0649). The TT genotype of C393T becomes significant (HR=1.291, p=0.0467) and the TT genotype of C2273T remains significant (HR=1.402, p<0.0273) in a multivariate model, including history of non-sustained VT (NSVT), left ventricular ejection fraction (LVEF), QRS duration, gender and history of ischemic cardiomyopathy.

A log likelihood test was performed to compare final models with and without SNP markers. When the nonmarker model was compared to the model with a variable indicating that the patient has genotype TT for either C393T or C2273T, the p-value was 0.00055. GNAS c.393 C>T (TT) is around 10,000 nucleotides away from the haplotype and is moderately linked. These results are consistent with Frey et al., EUROPEAN HEART JOURNAL (2011). The Frey publication disclosed a study of patients after Coronary artery bypass grafting (CABG). In that population, the C2273T SNP was in a haplotype that was predictive of 1 year cardiovascular-related mortality, wherein the *3 haplotype was protective and the *1 haplotype was the riskiest of the 3 haplotypes. In DISCOVERY, the C allele of the C2273T SNP was associated with risk of both all-cause mortality and cardiac-related mortality. Within the DISCOVERY cohort the C2273T T allele leads to increased VT/VF risk, while the C allele simultaneously leads to mortality and cardiac-related mortality risk. Without being limited to any particular theory of invention, it is believed that the TT genotypes for either of the two genes are indicative of an increased risk of VT/VF.

The Essen Pilot Study, "Better identification of patients who benefit from implantable cardioverter defibrillators by genotyping the G protein 3 subunit (GNB3) C825T polymorphism," Wieneke et al., Institute of Pharmacogenetics and Department of Cardiology, University of Duiburg-Essen, Germany, included 82 patients, 23 of whom experienced at least 1 episode, for a total of 75 episodes. The TT/CT versus CC resulted in HR 3.9 (95% CI 1, 6-9, 7).

Log likelihood tests comparing the models with and without the C393T (rs7121) TT genotype (p=0.002) or either of the TT GNAS genotypes (p=0.0002) can indicate possible significant model improvement. Within the subgroup of subjects with a history of ischemic cardiomyopathy, the C393T (rs7121) TT genotype remained as a significant predictor of time to VT (HR=1.76, p<0.0006) while in subjects with a history of non-ischemic cardiomyopathy, the C2273T TT genotype remained a significant predictor of time to VT (HR=1.8, p=0.05). As such, the GNAS gene contains 2 SNPs that improve prediction of time to VT beyond other known and suspected clinical factors.

In the genetic portion of the DISCOVERY study, candidate gene polymorphisms involved in coding of the G-protein subunits were correlated with the occurrence of ventricular arrhythmias in patients receiving an ICD for primary prevention. Seven specific SNPs that were tested are listed in Table 2.

The patients were primary prevention patients from whom blood samples were collected. After two years, follow-up was performed to determine whether patients had experienced a VT/VF event (the "event group"), or not (the "control group"). VT/VF refers to ventricular tachycardia (VT) and ventricular fibrillation (VF). VT is an increased heart rate, originating from the ventricles, the bottom chambers of the heart. VT may lead to VF, which is an uncoordinated contraction of the heart ventricles causing improper contractions. In turn, if not immediately treated, this can lead to asystole (flatline) or a complete stop of blood circulation, which can result in death of the patient within minutes. Death due to VT or VF may be commonly referred to as sudden cardiac death (SCD) or sudden cardiac arrest (SCA).

As described herein, 1,145 primary prevention patients were ultimately included in an analysis cohort of genotyped patients with device interrogation information to confirm any potential VT/VF events. FIG. 1 shows the study design, which involved enrollment of patients who have no previous history of lethal arrhythmias, but are indicated for ICD implant because of elevated risk of lethal arrhythmias. FIG. 4 indicates details of the study execution. Of those, during the study follow-up period, 848 were part of the control group (no VT/VF event, as determined by blinded physician adjudication) while 297 were in the event group (a VT/VF event did occur). The variables that were measured for each patient over the course of the study include: age, gender, LVEF (%), NYHA Class, QRS Duration (msec), cardiomyopathy etiology (ischemic/non-ischemic cardiomyopathy), history of non-sustained ventricular tachycardia (NSVT), history of atrial fibrillation, history of premature ventricular complexes (PVC), history of syncope, history of diabetes, use of beta blockers, use of anti-arrhythmic medications, use of diuretics, use of ACE inhibitors, use of cardiac glycoside, use of antilipidemics, GNAS c.393 C>T (CC/CT versus TT) and GNAS c.2273 C>T. The prevalence of each of these variables, and the number of patients with each variable that experienced a VT episode, is shown in Table 3, along with p-values for each variable.

TABLE 2

SNPs tested as part of the DISCOVERY study

| Gene | SNP | Chr. | RS number | SNP with 25 bp flanking sequences | SEQ ID No. |
|---|---|---|---|---|---|
| GNAS | c.393 C > T | 20q13.3 | rs7121 | agaaccagttcagagtggactacat[c/t]ctgagtgtgat gaacgtgcctgact | |
| | c.2273 C > T | | rs12481583 | ttgcctctggcctaggaatctgcag[c/t]ttaagccagtg acacaatattttgc | 2 |
| | c.2291 C > T | | rs6026584 | tctgcagcttaagccagtgacacaa[t/c]attttgcattttt aaatggtgattc | 3 |
| GNAQ | c.382 G > A | 9q21 | | gccgccaggcgcacggcgtagggga[g/a]cctcgca ggcggcggcggcggcggc | 4 |
| | c.387 G > A | | | ctctcgccgccaggcgcacggcgta[g/a]gggagcct cgcaggcggcggcggcg | 5 |
| | c.908/909 GC > TT | | | ctgagtgtgatgaacgtgcctgact[gc/tt]ccagcccg ggagccgcgcgggcgag | 6 |
| GNB3 | c.825 C > T | 12p13 | | agagcatcatctgcggcatcacgtc[c/t]gtggccttctc cctcagtggccgcc | 7 |

TABLE 3

| Variable | VT Episodes No (n = 848) | VT Episodes Yes (n = 297) | p-value | Total Patients (n = 1145) |
|---|---|---|---|---|
| Age (years) | | | 0.7257 | |
| Mean ± Standard Deviation | 61.7 ± 11.1 | 61.4 ± 10.3 | | 61.6 ± 10.9 |
| Number of Patients with Measure Available (N, %) | 848 (100.0%) | 297 (100.0%) | | 1145 (100.0%) |
| Gender (N, %) | | | 0.0401 | |
| Male | 701 (82.7%) | 262 (88.2%) | | 963 (84.1%) |
| Female | 147 (17.3%) | 35 (11.8%) | | 182 (15.9%) |
| Diabetic | 268 (31.6%) | 105 (35.4%) | 0.2751 | 373 (32.6%) |
| Missing | 4 (0.5%) | 0 (0.0%) | | 4 (0.3%) |
| Medical History of | | | | |
| Non-sustained VT | 207 (24.4%) | 114 (38.4%) | <.0001 | 321 (28.0%) |
| Missing | 1 (0.1%) | 0 (0.0%) | | 1 (0.1%) |
| Atrial fibrillation | 168 (19.8%) | 59 (19.9%) | 0.6854 | 227 (19.8%) |
| Missing | 1 (0.1%) | 0 (0.0%) | | 1 (0.1%) |
| Cardiomyopathy etiology | | | 0.0042 | |
| Ischemic | 495 (58.4%) | 143 (48.1%) | | 638 (55.7%) |
| Dilated | 220 (25.9%) | 104 (35.0%) | | 324 (28.3%) |
| Hypertrophic | 36 (4.2%) | 10 (3.4%) | | 46 (4.0%) |
| Restrictive | 1 (0.1%) | 2 (0.7%) | | 3 (0.3%) |
| Missing | 96 (11.3%) | 38 (12.8%) | | 134 (11.7%) |
| QRS Width (ms) | | | 0.0418 | |
| Mean ± Standard Deviation | 106.9 ± 24.5 | 110.6 ± 23.2 | | 107.9 ± 24.2 |
| Number of Patients with Measure Available (N, %) | 772 (91.0%) | 274 (92.3%) | | 104 (91.4%) |
| Documented events prior to enrollment | | | | |
| Premature ventricular complexes | 131 (15.4%) | 58 (19.5%) | 0.0886 | 189 (16.5%) |
| Missing | 1 (0.1%) | 0 (0.0%) | | 1 (0.1%) |
| Syncope | 67 (7.9%) | 29 (9.8%) | 0.3482 | 96 (8.4%) |
| Missing | 1 (0.1%) | 0 (0.0%) | | 1 (0.1%) |
| LVEF (%) | | | 0.2147 | |
| Mean ± Standard Deviation | 29.4 ± 10.0 | 28.8 ± 10.4 | | 29.3 ± 10.1 |
| Number of Patients with Measure Available (N, %) | 828 (97.6%) | 292 (98.3%) | | 1120 (97.8%) |
| NYHA Class (N, %) | | | 0.2198 | |
| None | 19 (2.2%) | 6 (2.0%) | | 25 (2.2%) |
| I | 84 (9.9%) | 23 (7.7%) | | 107 (9.3%) |
| II | 492 (58.0%) | 178 (59.9%) | | 670 (58.5%) |
| III | 230 (27.1%) | 86 (29.0%) | | 316 (27.6%) |
| IV | 13 (1.5%) | 2 (0.7%) | | 15 (1.3%) |
| Missing | 10 (1.2%) | 2 (0.7%) | | 12 (1.0%) |
| Medication at Enrollment (N, %) | | | | |
| ACE inhibitor | 710 (83.7%) | 258 (86.9%) | 0.2725 | 968 (84.5%) |
| Beta blocker | 757 (89.3%) | 260 (87.5%) | 0.592 | 1017 (88.8%) |
| Anti-arrhythmic | 124 (14.6%) | 39 (13.1%) | 0.8136 | 163 (14.2%) |
| Diuretic | 177 (20.9%) | 57 (19.2%) | 0.1881 | 234 (20.4%) |
| Cardiac glycoside | 86 (10.1%) | 38 (12.8%) | 0.1253 | 124 (10.8%) |
| Anti-lipidemics | 589 (69.5%) | 204 (68.7%) | 0.4259 | 793 (69.3%) |
| TT for either C393T or C2273T | | | <.0001 | |
| No | 592 (69.8%) | 167 (56.2%) | | 759 (66.3%) |
| Yes | 256 (30.2%) | 130 (43.8%) | | 386 (33.7%) |

The collected data on the 1,145 patients were analyzed using both a univariate and a multivariate analysis, as shown in Table 4. As used in the first through thirteenth aspects of the invention and understood by those of ordinary skill in the art, multivariate analysis means that all the measured variables were analyzed simultaneously. In the present DIS-COVERY study, Cox regression was implemented for the multivariate analysis. Variables included in the multivariate model included: age, gender, LVEF (%), NYHA Class, QRS Duration (msec), heart failure etiology (ischemic/non-ischemic cardiomyopathy), history of non-sustained ventricular tachycardia (NSVT), history of atrial fibrillation, history of premature ventricular complexes (PVC), history of syncope, history of diabetes, use of beta blockers, use of anti-arrhythmic medications, GNAS c.393 C>T (CC/CT versus TT) and GNAS c.2273 C>T (CC/CT versus TT).

TABLE 4

Summary of results of univariate and multivariate analysis

| Parameter | Comp Group | Univariate p-value | Univariate HR | Multivariate p-value | Multivariate HR |
|---|---|---|---|---|---|
| Non-sustained VT | Y | <.0001 | 1.8 | <.0001 | 1.895 |
| Ischemic Cardiomyopathy | Y | 0.0042 | 0.74 | 0.008 | 0.698 |
| QRS width | | 0.0418 | 1.01 | 0.026 | 1.005 |
| C2273T (TT vs CC/CT) | TT | 0.0019 | 1.57 | 0.0273 | 1.402 |
| Gender | Male | 0.0401 | 1.45 | 0.0372 | 1.465 |

TABLE 4-continued

Summary of results of univariate and multivariate analysis

| Parameter | Comp Group | Univariate p-value | HR | Multivariate p-value | HR |
|---|---|---|---|---|---|
| LVEF |  | 0.2147 | 0.99 | 0.0456 | 0.987 |
| C393T (TT vs CC/CT) | TT | 0.0048 | 1.42 | 0.0467 | 1.291 |
| Anti-arrhythmics | Y | 0.8136 | 0.96 | 0.0799 | 0.726 |
| NYHA Class |  | 0.2198 | 1.11 | 0.2312 | 1.114 |
| Diabetes | Yes | 0.2751 | 1.14 | 0.2544 | 1.154 |
| Age |  | 0.7257 | 1 | 0.4663 | 0.996 |
| Beta blockers | Y | 0.592 | 0.91 | 0.4701 | 0.876 |
| Syncope | Y | 0.3482 | 1.2 | 0.6001 | 1.114 |
| Atrial fibrillation | Y | 0.6854 | 1.061 | 0.8699 | 1.025 |
| Premature ventricular complexes | Y | 0.0886 | 1.28 | 0.6944 | 1.062 |

Univariate analysis was performed where a single variable is compared for the control and event groups at a time. The hazard ratio (HR) of each variable was calculated. In particular, the HR is defined as the ratio of the hazard rates for a variable between the control and event groups. For example, in Table 4, the HR for NSVT is 1.8 meaning that when a patient has experienced Non-sustained Ventricular Tachycardia (NSVT), the chance of that patient experiencing a VT/VF event (chance of ending up in the event group) is 1.8 times higher than that patient does not experience a VT/VF event (ending up in the control group) over the course of this study. The HR is a relative measure of risk and not an absolute measure. Detailed description of the variables provided in Tables 4 follow:

(1) "NSVT" is non-sustained ventricular tachycardia. General tachycardia from the Greek for "fast heart" is defined as a heart rate faster than the normal average rate of 100 beats per minute (bpm). NSVT is defined as three or more consecutive beats at a rate in excess of 120 bpm, and lasting less than 30 seconds. Tachycardia may be asymptomatic. If it is pathogenic (causes disease symptoms), it is referred to tachyarrhythmia. A ventricular tachyarrhythmia is pathogenic tachycardia originating from the left ventricle.

(2) "LVEF" refers to left ventricular ejection fraction, and to the percentage of the total volume of blood in the left ventricle that is actually pumped out of the heart when beating. The human heart consists of four separate chambers, a right atrium and ventricle, and a left atrium and ventricle. The atria receive blood from the circulation and pump it into the ventricles. The more powerful ventricles pump blood into the circulation. The right side of the heart receives blood from the rest of the body and pumps it into the lungs. The heart's left side receives the now oxygenated blood from the lungs and pumps it towards the rest of the body. If the LVEF is <40% in ischemic patients NSVT has been associated with an increased risk of SCD, further testing is recommended to determine whether an ICD should be implanted.

(3) "QRS duration" refers to the temporal length of the QRS complex in a portion of a typical human electrocardiogram. In general, the electrocardiogram has five deflections, or peaks and troughs, named P, Q, R, S and T. R refers to the characteristic high peak, and Q and S are the troughs that immediately precede and follow this peak, respectively. Q, R and S occur rapidly after each other, and are referred to as the QRS complex. QRS duration (typically 0.06-0.12 seconds) may be shortened with tachycardia. It is noted that QRS duration can sometimes be longer with VTs as compared to normal heart rhythm.

(4) "HF etiology—Ischemic" refers to the cause (etiology) of heart failure (HF), in this case ischemia (ischemic cardiomyopathy). Ischemia is the restriction of blood flow to tissues and in the first through thirteenth aspects of the invention within the context of heart muscle. Patients reporting a history of ischemic cardiomyopathy are compared to patients reporting a history of non-ischemic cardiomyopathy and patients reporting no history of cardiomyopathy.

(5) "Gender (Male)": DISCOVERY studied whether being male (as opposed to female) imposed an increased risk of ventricular tachyarrhythmia.

(6) "GNAS c.393 C>T (TT)" refers to a genetic polymorphism in the GNAS gene (rs7121). GNAS refers to the human GNAS complex locus (Entrez Gene ID 2778). The GNAS gene encodes the G protein alpha subunit that is part of the so-called "s" signaling pathway (others being the "q" and "i/o" pathways). G proteins consist of three subunits called alpha, beta and gamma, encoded by separate genes, and are coupled to extracellular receptors that detect signals from outside a cell. The alpha subunit of GNAS is the activating component. In response to an extracellular signal the alpha subunit is activated and in turn activates the G-protein and a downstream signaling cascade, ultimately resulting in, for example, a physiological change in the cell. From one human individual to the next, small differences in the genetic code may exist. These are referred to as single-nucleotide polymorphisms, or SNPs. Such a SNP may cause a mutation in the encoded protein or be silent (not cause a mutation), or alter the expression level of the gene. GNAS c.393 refers to a specific nucleotide in the sequence of the cDNA of the GNAS gene as measured from the start (origin) of the sequence. C>T refers to the actual variation that is observed. The reference ("normal") sequence contains a "C" in position 393, but in individuals with the polymorphism a "T" is found instead. Since humans have two copies of each gene, one originating from the father and one from the mother (the notable exception being the sex chromosomes, X and Y, in males), three different "profiles" of SNPs are possible in any individual: two Cs, or CC, two Ts, or TT, or one C and one T, or CT. In the first through thirteenth aspects of the invention, it was thus determined whether having a TT profile (as opposed to CC or CT) carries an increased risk of ventricular tachyarrhythmia.

(7) "Copies of haplotype *2"—Haplotype refers to a set of SNPs that are generally inherited together as a block (i.e., they are statistically associated with one another). As such, if the sequence of one or a few of the SNPs is known, the sequences of other SNPs present in that same block can be inferred. For example, if the genotypes of SNP 2273 (i.e., rs12481583) and SNP 2291 (i.e., rs6026584) are known, the sequence of 6 other SNPs present in the same block can be inferred. Notably, the dbSNP identifiers of these other 6 SNPs are rs6123837, Del1340, rs6026580, rs6092704, rs12481574 and rs15754. As such, determining the sequence of SNPs 2273 (i.e., rs12481583) and 2291 (i.e., rs6026584) has the same value as determining the sequence of all eight SNPs in this block, as the remaining values can be inferred from the 2273 and 2291 sequences. Moreover, a correlation in the first through thirteenth aspects of the invention exists between the sequence identity of the 2273 and/or 2291 SNPs and the biological effect. The biological effect associated with the haplotype is not necessarily caused by these specific SNPs, but could be due to other sequences in the haplotype block. As such, methods relying on the identification of such haplotypes are contemplated by the first through thirteenth aspects of the invention. This means that determining the sequence of SNPs 2273 and 2291 has the same value as determining the sequence of all eight SNPs in this block, as the remaining values can be inferred from the 2273 and 2291 sequences.

Notably, an eight-variant region can be passed on as a block. Thus, with high likelihood, one can receive one set of the 8 variants from each parent because there are 3 potential sets of these variants that can be inherited together. Each individual will receive two copies of this set of variants (one from each parent). The numbers next to those sequences show the prevalence of each set of sequences. As an example, the first set of variants is referred to as the *1 haplotype and its prevalence is 32.5%. Because the numbers do not add up to exactly 100%, there can be other low prevalence haplotypes in addition to the three listed in Table 5.

TABLE 5

| Position | dbSNP identifier | *1 Variant | *2 Variant | *3 Variant | SEQ ID No. |
|---|---|---|---|---|---|
| −1211 | rs6123837 | G | G | A | 8 |
| 1340 | Del1340 (rs35813452) | I | I | D | 13 |
| 1368 | rs6026580 | C | T | T | 9 |
| 1696 | rs6092704 | A | A | A | 10 |
| 2025 | rs12481574 | G | G | A | 11 |
| 2273 | rs12481583 | C | C | T | 2 |
| 2291 | rs6026584 | T | C | C | 3 |
| 2445 | rs15754 | C | G | G | 12 |

Figure 6:
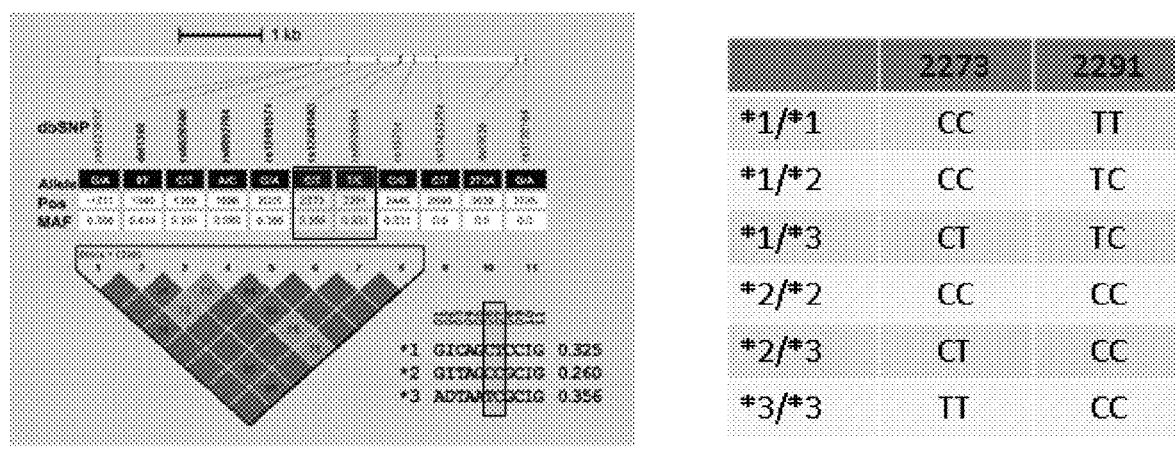
FIG. 6 is a figure adapted from Frey et al., EUROPEAN HEART JOURNAL (2009), showing that haplotypes can be identified by the 2273 and 2291 SNPs.

As shown in FIG. 6, "Haplotype *2" is an arbitrary denomination that can indicate a "C" configuration for 2273 as well as a "C" for 2291. In this particular case, the other possible haplotypes can be *1 (C for 2273 and T for 2291) and *3 (T for 2273 and C for 2291). The theoretical fourth option of T for 2273 and T for 2291 does not appear to occur within the cohort studied. In Table 5, Del1340 can be represented by rs35813452 for CGTGGTTTCTTTTTTTTTTTTTTTT[-/TTTTTTT/TTTTTTTTT]GTCCTCCTCAAGGTGGGAGGGGGGA (SEQ ID NO. 13) where the negative sign (−) represent a deletion, and TTTTTTT or TTTTTTTT further represent possible deletions.

FIG. 6 also shows the haplotypes of the GNAS SNPs of the first through thirteenth aspects of the invention. The left panel of FIG. 6 illustrates the eight SNPs in the GNAS gene from Table 5 that are inherited together as a block. rs12481583 refers to c.2273C>T and rs6026584 to c.2291T>C. The three right-most SNPs (rs13433254, Del3638, and rd3730164) are not part of the block, as indicated by the inverted triangle below the haplotype in FIG. 6. SNP rs7121 c.393C>T, also part of the first through thirteenth aspects of the invention, is not part of this block and is inherited independently of the eight SNPs in the Block 1 haplotype (see Table 6).

Three haplotypes (configurations) for the SNPs were reported in a study population, labeled *1, *2 and *3, with frequencies of occurrence of 0.325, 0.260 and 0.356, respectively. Without being limited to any particular theory of invention, it is noted that the three numbers do not sum to 1.0, or 100%, because additional, rarely occurring haplotypes may exist. The right panel summarizes all possible combinations of sequences for the 2273 and 2291 SNPs that may occur in an individual. For example, an individual with *1/*1 can receive a *1 block from each parent and will have two Cs for 2273 and two Ts for 2291. An individual with *1/*3 can receive a *1 block from one parent and a *3 block from the other parent, and will have one C and one T for 2273 and one T and one C for 2291.

Univariate analysis of the seven SNPs (3 genes coding for G-protein subunits: C825T in GNB3, GC(-909/-908)TT, G(-382)A and G(-387)A in GNAQ and C393T, C2273T and T2291C in GNAS) resulted in significant p-values for two of the seven SNPs, namely GNAS c.393C>T and GNAS c.2273C>T (0.0048 and 0.0019, respectively) as shown in Table 6. The prevalence of each SNP during the study is shown in Table 7.

TABLE 6

Summary of results with regard to SNPs, after univariate analysis - SNPs modeled as categorical variables

| Variable | Genotype Reference | Genotype Comparison | HR | p-value |
|---|---|---|---|---|
| GNAS c.393 C > T | CC | CT | 1.074 | 0.6392 |
| | | TT | 1.495 | 0.0128 |
| GNAS c.2273 C > T | CC | CT | 1.143147 | 0.2959 |
| | | TT | 1.684 | 0.00080014 |
| GNAS c.2291 C > T | CC | CT | 0.867 | 0.2462 |
| | | TT | 0.932 | 0.7277 |
| GNAQ c.382 G > A | GG | AG | 0.778 | 0.1328 |
| | | AA | 0.708 | 0.6270 |
| GNAQ c.387 G > A | GG | AG | 1.155 | 0.4678 |
| | | AA | 0.000 | 0.9747 |
| GNAQ c.908/909 GC > TT | GC/GC | GC/TT | 1.057 | 0.6831 |
| | | TT/TT | 1.086 | 0.6106 |
| GNB3 c.825 C > T | CC | CT | 1.079 | 0.5329 |
| | | TT | 0.945 | 0.7935 |

TABLE 7

| SNP | Allele Frequency Major | Allele Frequency Minor | Genotype Frequency M/M | Genotype Frequency M/m | Genotype Frequency m/m |
|---|---|---|---|---|---|
| GNAS_Cp2273T | 63.10% | 36.90% | 39.83% | 46.55% | 13.62% |
| GNAS_Cp2291T | 68.21% | 31.79% | 46.03% | 44.37% | 9.61% |
| GNAS_Cp393T | 49.13% | 50.87% | 24.89% | 48.47% | 26.64% |
| GNB3_Cp825T | 68.60% | 31.40% | 46.81% | 43.58% | 9.61% |
| GNAQ_Gm382A | 90.79% | 9.21% | 82.53% | 16.51% | 0.96% |
| GNAQ_Gm387A | 95.33% | 4.67% | 90.92% | 8.82% | 0.26% |
| GNAQ_GCm909m908TT | 53.71% | 46.29% | 29.87% | 47.69% | 22.45% |

Table 8 provides an ordinal analysis of p-values wherein each SNP has been considered as having a numeric value wherein the ordinal value is shown as the number of the minor allele. Hence, the notation of GNAS c.### X>Y indicates that Y is the minor allele and the ordinal value. For example, GNAS c.393 C>T is where CC=0, CT=1 and TT=2 resulting in a raw p-value of 0.00901. In particular, the C393T genotype could be set up as a categorical variable with three categories (CC, CT, TT). Alternatively, the C393T genotype could be set up as a continuous (ordinal) variable, as is the case for the analysis for Tables 8 and 9. The ordinal values could be thought to represent the number of minor (less common) alleles. Since T is the minor allele, ordinal coding would be CC=0, CT=1, TT=2. The ordinal genotype is fit in the Cox Regression as a continuous (as opposed to categorical) variable.

TABLE 8

Summary of results with regard to SNPs, after univariate analysis - SNPs modeled as ordinal variables

| | | p-values | |
|---|---|---|---|
| Variable | HR | Raw | Perm |
| GNAS c.393 C > T | 1.238 | 0.009 | 0.0557 |
| GNAS c.2273 C > T | 1.279 | 0.003 | 0.0163 |
| GNAS c.2291 C > T | 1.068 | 0.465 | 0.9875 |
| GNAQ c.382 G > A | 0.784 | 0.114 | 0.5466 |
| GNAQ c.387 G > A | 1.136 | 0.504 | 0.9916 |
| GNAQ c.908/909 GC > TT | 1.053 | 0.519 | 0.9929 |
| GNB3 c.825 C > T | 1.013 | 0.884 | 1 |

Table 10 shows an ordinal analysis for SNPs modeled as recessive TT for C393T and C2273T. The results demonstrate low p-value for GNAS c.393 C>T and GNAS c.2273 C>T.

TABLE 9

| Variable | HR | P-value |
|---|---|---|
| GNAS c.393 C > T | 1.424 | 0.0042 |
| GNAS c.2273 C > T | 1.562 | 0.0022 |

The VT incidence at 24 months post enrollment for each gene is shown in Table 10. The two SNPs were associated with an increased risk of VT. After correction for multiple comparisons, GNAS c.2273 remained significant while GNAS c.393 was borderline significant. While on the same GNAS gene, these SNPs appear to be relatively independent. The fact that the TT genotype appears to have increased incidence of VT from the CC and CT genotypes, which appear to have similar incidence of VT, suggests that it is a recessive trait. The same data is shown as Kaplan Meier plots in FIG. 5. The Kaplan-Meier estimate for VT/VF incidence at 24 months in 305 patients (26.6%) with TT genotype in C393T was 41.1% (95% confidence interval of 34.7%-48.1%), while the incidence in patients with CC/CT genotypes was 30.9% (95% confidence interval of 27.3%-34.9%). The Kaplan-Meier estimate for VT/VF incidence at 24 months in 156 patients (13.6%) with TT genotype in C2273T was 45.3% (95% confidence interval of 36.7%-54.8%) and for patients with CC/CT genotypes was 31.6% (95% confidence interval of 28.2%-35.3%). This increased risk remained significant after adjustment for non-genetic covariates, including history of non-sustained VT, ischemic cardiomyopathy etiology, left ventricular ejection fraction, QRS duration and gender, as shown in Table 4.

TABLE 10

| | PPV (Incidence @ 2 years) | 95% Confidence Interval |
|---|---|---|
| GNAS_393_TRec | | |
| CC/CT | 30.9% | 27.3%-34.9% |
| TT | 41.1% | 34.7%-48.1% |
| GNAS_2273_TRec | | |
| CC/CT | 31.6% | 28.2%-35.3% |
| TT | 45.3% | 36.7%-54.8% |

Figure 8:
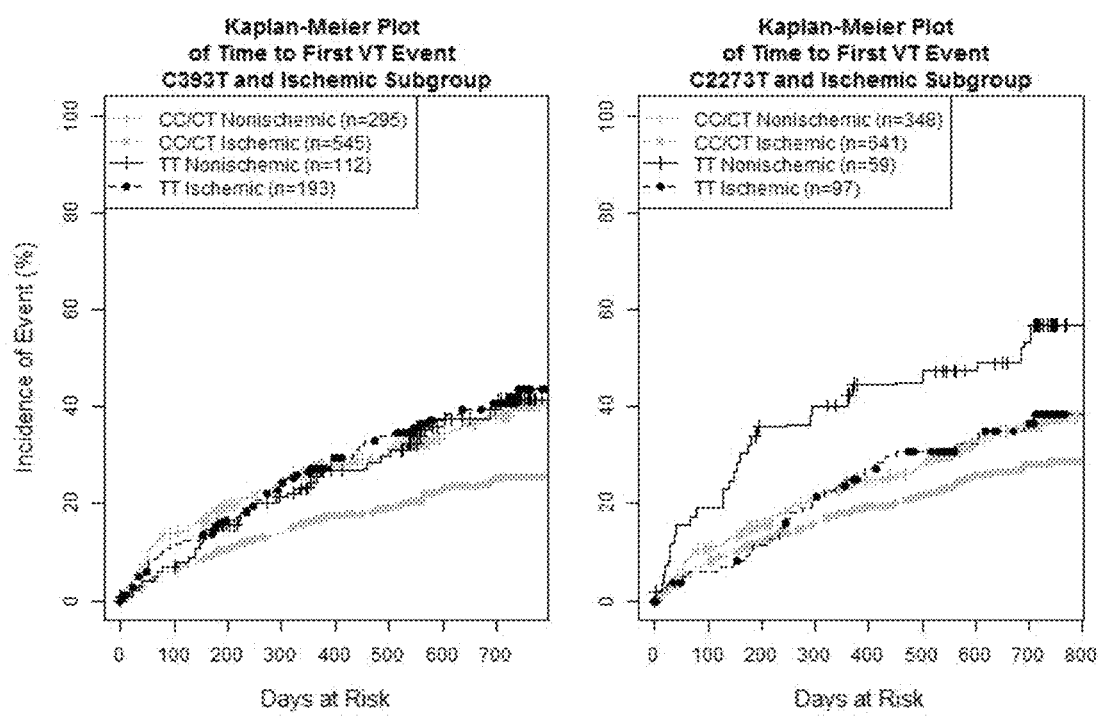
FIG. 8 shows arrhythmia events in subjects with history of ischemic and nonischemic cardiomyopathy in a Kaplan Meier plot of the incidence of event (arrhythmia) against the number of days at risk.

Further analysis was performed for the data relating to the C393T and C2273T SNPs. In particular, the combined effect of every variation of the two SNPs on the incidence of an event was analyzed, where patients with a history of ischemic cardiomyopathy were separated from those with a history of non-ischemic cardiomyopathy as shown in FIG. 8. FIG. 8 corresponds to Tables 11 and 12. In particular, because history of non-ischemic cardiomyopathy (HF etiology) was a significant variable in the multivariate model (Table 4), separate subgroup analyses were performed on patients with history of ischemic cardiomyopathy and non-ischemic cardiomyopathy.

TABLE 11

| Variable | HR | p-value |
|---|---|---|
| Summary of results after multivariate analysis - patients reporting history of ischemic cardiomyopathy for GNAS c.393 | | |
| NSVT | 2.012 | 0.0003 |
| Anti-arrhythmic medication | 0.426 | 0.0161 |
| GNAS c.393 C > T (TT) | 2.078 | <.0001 |
| Summary of results after multivariate analysis - patients reporting history of non-ischemic cardiomyopathy for GNAS c.2273 | | |
| NSVT | 1.975 | 0.0004 |
| LVEF | 0.983 | 0.0253 |
| GNAS c.2273 C > T (TT) | 1.796 | 0.0109 |

FIG. 8 shows arrhythmia events in subjects with history of ischemic cardiomyopathy as a Kaplan Meier plot of the incidence of event (arrhythmia) against the number of days at risk for each gene. As shown in FIG. 8 and corresponding Table 11, GNAS c.393 C>T (TT) is significant in the multivariate analysis (HR=2.078, p-value=p<0.0001).

Data for overall and ischemic or non-ischemic subgroup counts of subjects with each genotype combination are provided in Table 13. These data are in conjunction with FIGS. 7-8. Some patients did not report any history of cardiomyopathy. Hence, it will be understood that the number of ischemic and non-ischemic patients do not necessarily add up to the overall number of patients within genotype groups.

TABLE 13

Subgroup counts of subjects with each genotype combination.

| C393T | C2273T | Overall | Ischemic | Non-ischemic |
|---|---|---|---|---|
| CC | CC | 170 | 85 | 63 |
| CC | CT | 94 | 53 | 30 |
| CC | TT | 20 | 10 | 8 |
| CT | CC | 210 | 128 | 61 |
| CT | CT | 282 | 158 | 88 |
| CT | TT | 61 | 33 | 17 |
| TT | CC | 75 | 45 | 25 |

TABLE 13-continued

Subgroup counts of subjects with each genotype combination.

| C393T | C2273T | Overall | Ischemic | Non-ischemic |
|---|---|---|---|---|
| TT | CT | 152 | 86 | 47 |
| TT | TT | 75 | 38 | 28 |

As shown in Table 11, GNAS c.393 C>T (TT) is very significant in the multivariate analysis in the subgroup of ischemic patients (p<0.001). These are the occurrence of NSVT (non-sustained ventricular tachycardia), a non-genetic factor, and the presence of the "TT" genotype for the GNAS c.393C>T SNP, a genetic factor. The HR for NSVT is 1.895, which indicates that patients positive for NSVT have an almost 2× higher chance of ending up in the "event" group than of ending up in the "control" group. The HR for the GNAS 393 SNP is 1.291, indicating a 1.291× increased chance of experiencing ventricular arrhythmia when a patient has the TT variant of this SNP. As such, this finding can indicate the presence of the TT variety of the GNAS c.393C>T SNP as a predictor of ventricular arrhythmia.

Both SNPs studied remain significant in the multivariate model. Many of the other potential predictors of VT are outside of the p<0.05 range for predictive value.

Table 6 also shows that TT variants of the SNPs c.393C>T and c.2273C>T in the GNAS gene both are significant predictors of a VT/VF event. This may indicate the presence of the TT variety of the GNAS c.393C>T and c.2273C>T SNPs as predictors of ventricular arrhythmia.

Figure 9:
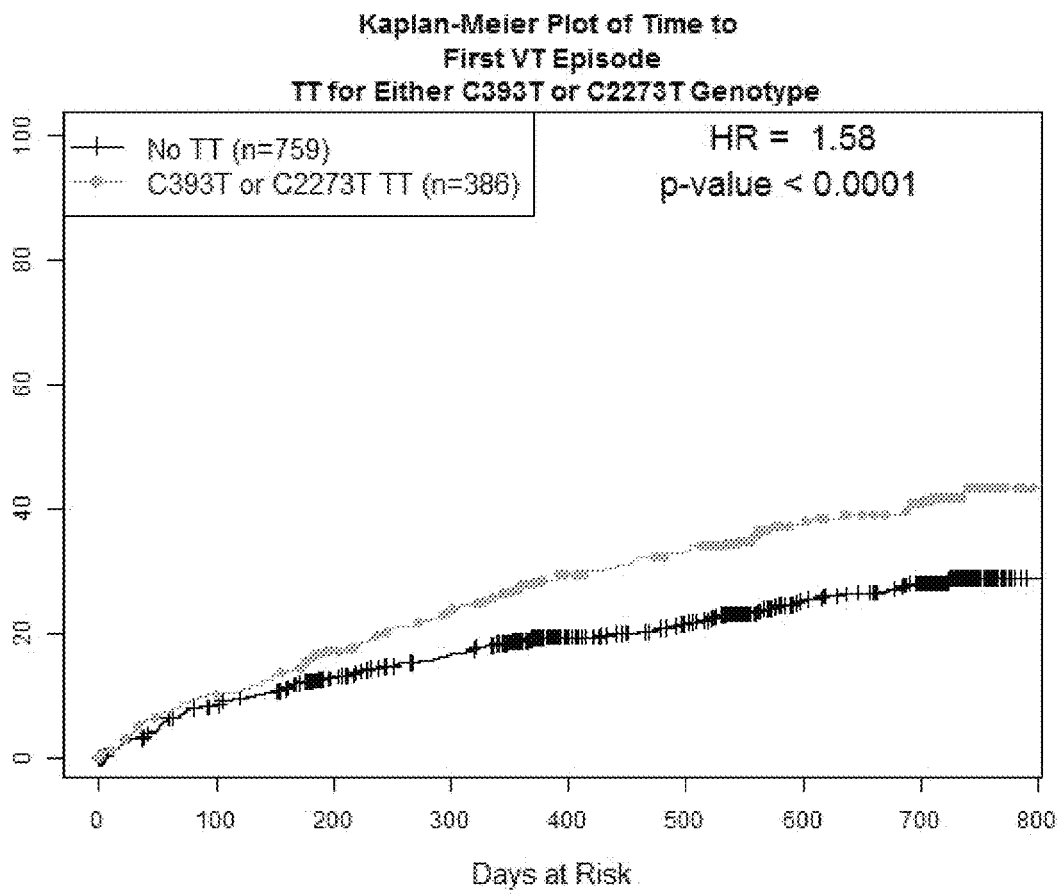
FIG. 9 is a plot showing the results of the DISCOVERY study for the homozygosity of the T allele in either GNAS c393 C>T or GNAS c2273 C>T as incidence of event over days at risk.

However, in the specific context of a patient history of ischemic versus non-ischemic cardiomyopathy, the predictive value of the two SNPS, C393T and C2273T, can be different. For example, FIG. 8 shows that in a population with a history of ischemic cardiomyopathy, there is a discernible separation between the Kaplan Meier curves representing the ischemic C393T CC/CT patients and the ischemic C393T TT patients, with the C393T TT patients having relatively higher risk of a VT/VF event. There is no discernible separation between the C393T genotypes in non-ischemic patients. FIG. 9 shows that patients with the TT genotype for C2273T have increased risk of VT/VF regardless of cardiomyopathy etiology. The occurrence of a TT sequence for either the C393T or the C2273T (the thick lines) can be associated with an increased incidence rate which appears about equal for each combination, with the possible exception of CC/TT and TT/CC, which may have a lower incidence. In contrast, patients with any of the other combinations that specifically do not include a TT sequence for either SNP (the thin lines) show a lower incidence rate. In the non-ischemic population, FIG. 8, the three long-dashed lines (TT variants of C2273T) show a higher incidence of events, but not any of the other lines (TT variants of C393T).

Haplotypes and haplotype pairs were identified by the C2291T and C2273T SNPs as shown in Tables 14 and 15 below and as described herein and in FIG. 6.

TABLE 14

| Haplotypes | c.2273 | c.2291 |
|---|---|---|
| *1/*1 | CC | TT |
| *1/*2 | CC | TC |
| *1/*3 | CT | TC |

TABLE 14-continued

| Haplotypes | c.2273 | c.2291 |
|---|---|---|
| *2/*2 | CC | CC |
| *2/*3 | CT | CC |
| *3/*3 | TT | CC |

TABLE 15

Haplotype Pairs

| | Frey (2009)* | | DISCOVERY | |
|---|---|---|---|---|
| Haplotype pair | N | % | N | % |
| *1/*1 | 86 | 10.8 | 113 | 9.7 |
| *2/*1 | 176 | 22.0 | 239 | 20.6 |
| *2/*2 | 59 | 7.4 | 114 | 9.8 |
| *3/*1 | 182 | 22.8 | 278 | 23.9 |
| *3/*2 | 207 | 25.9 | 257 | 22.1 |
| *3/*3 | 90 | 11.3 | 161 | 13.9 |

Figure 7:
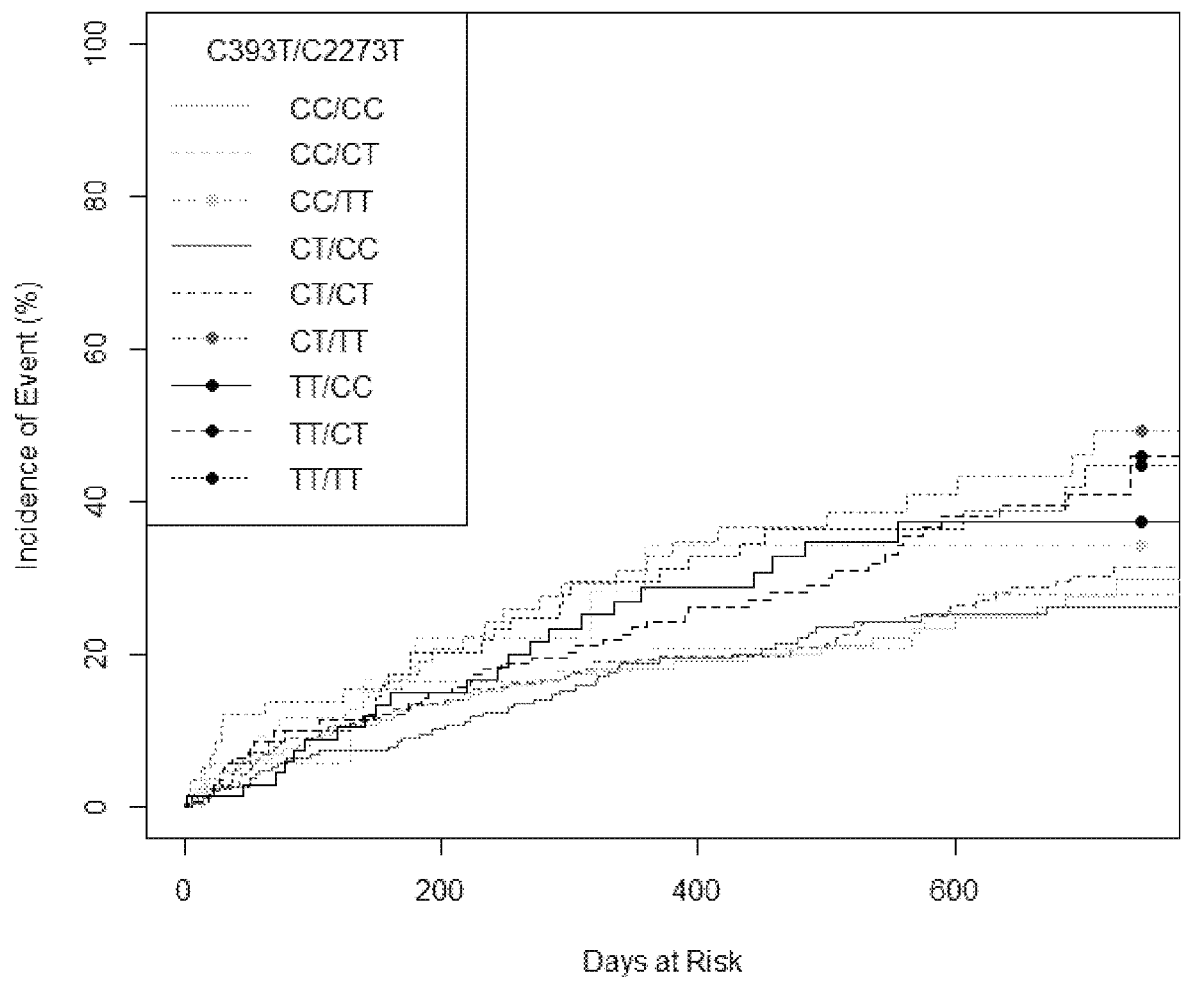
FIG. 7 is a plot showing the results of the DISCOVERY study for the combined genotype pairs for GNAS c393 C>T and GNAS c2273 C>T as incidence of event over time to first fast VT or last visit.

The incidence of event from the time to first fast VT or last visit for C393T/C2273T genotypes are shown in FIG. 7. The incidence of event from the time to first fast VT or last visit for the TT combined on either gene is shown in FIG. 9. As compared to patient population reported by haplotype in Frey et al., Table 15 demonstrates that the patient populations of the first through thirteenth aspects of the invention have similar haplotype distributions.

Figure 10:
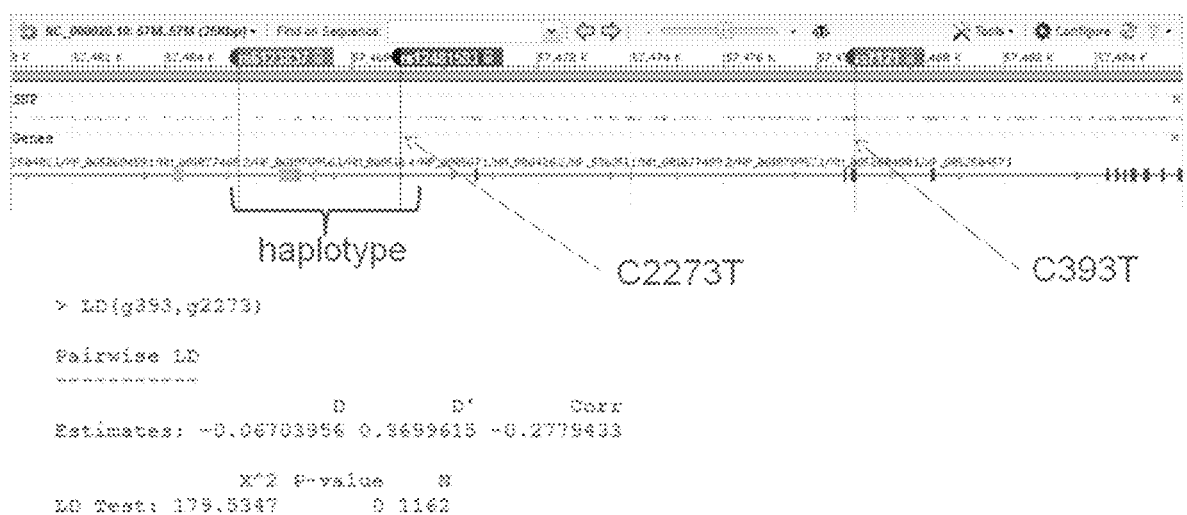
FIG. 10 shows the locations of GNAS c393 C>T or GNAS c2273 C>T in the genetic sequence and the distances between them.
Figure 16:
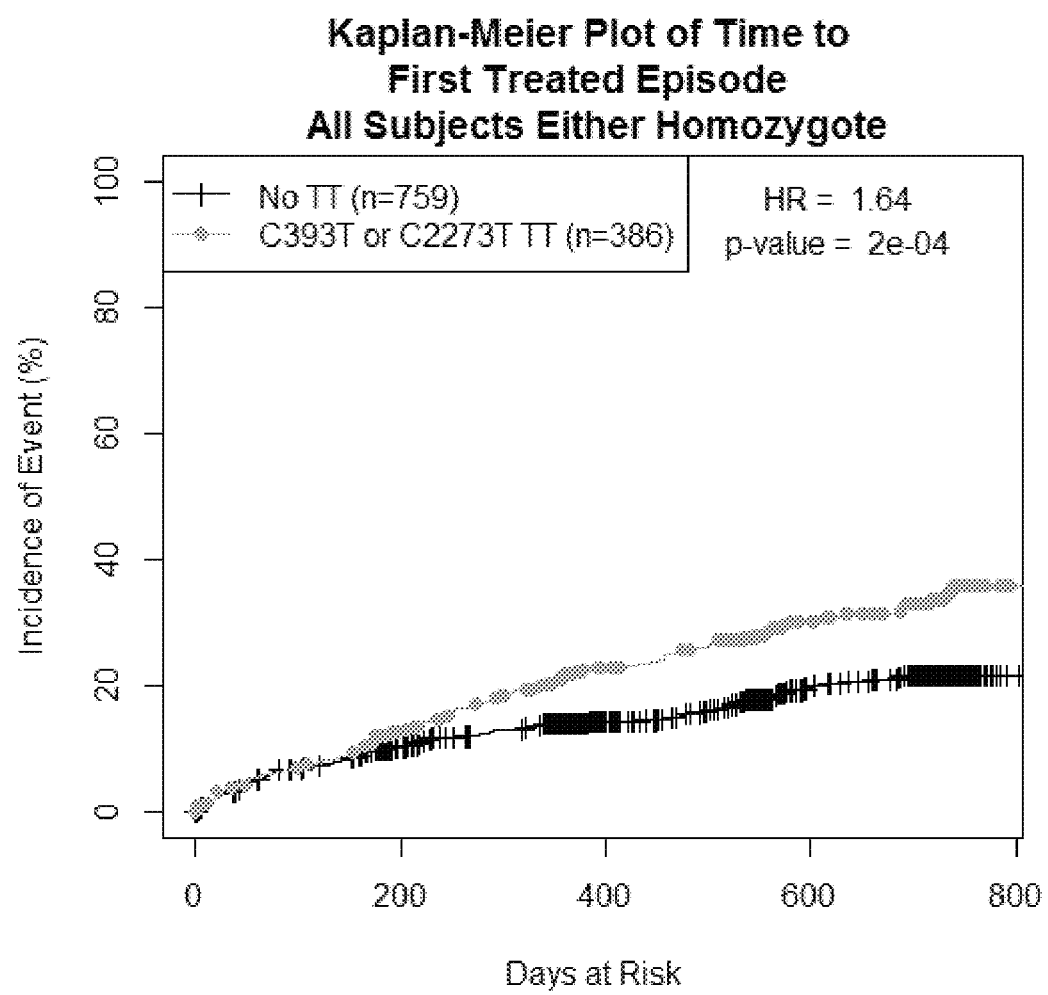
FIG. 16 shows a plot showing the results of the DISCOVERY study for the homozygosity in either GNAS c393 or GNAS c2273 as first treated episode over days at risk.

One phenomenon of SNPs is linkage disequilibrium, which refers to the tendency of specific alleles at different genomic locations to occur together more frequently than would be expected by random change. Alleles at given loci are said to be in complete equilibrium if the frequency of any particular set of alleles (or haplotype) is the product of their individual population frequencies. Several statistical measures can be used to quantify this relationship. Calculation of linkage disequilibrium between the two loci showed that they were not independent, however only a weak correlation was found (r=−0.2770825). The DISCOVERY design paper indicated that G-1211A would be among the SNPs genotyped. However, as it is in complete linkage disequilibrium with C2273T and the latter is easier to genotype, the decision was made to genotype C2273T. FIG. 10 shows the locations of the genes and the distances between them. Homozygosity for the T allele in either C393T or C2273T ($T_H$) was associated with a HR of 1.58, as shown in FIG. 16 (p=0.0001). The incremental value of $T_H$ was assessed by comparing models with all non-SNP covariates with and without $T_H$ and found to be statistically significant (p=0.00055). Patients having the TT genotype at both C393T and C2273T did not have increased risk compared to patients having the TT genotype at only one of those two loci.

Figure 11:
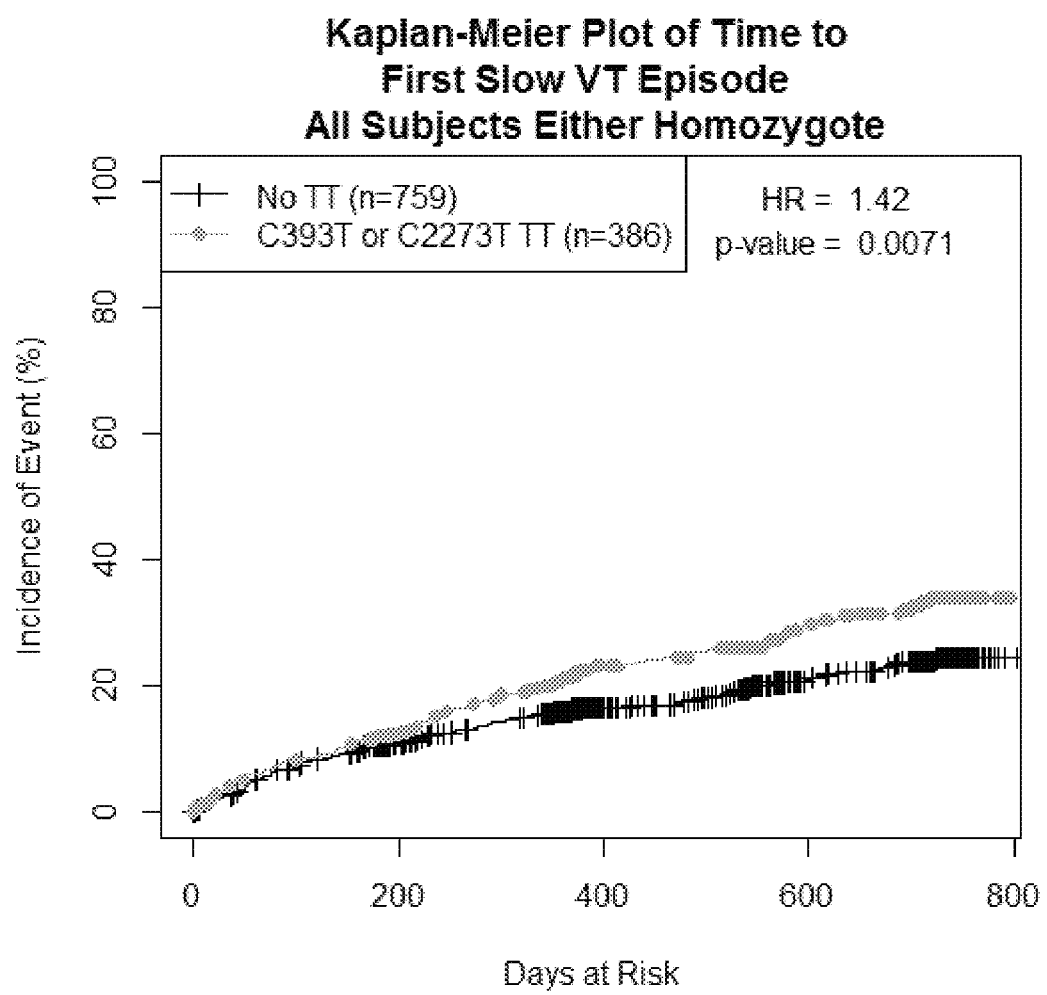
FIG. 11 shows a plot showing the results of the DISCOVERY study for the homozygosity in either GNAS c393 C>T or GNAS c2273 C>T as incidence of Slow VT zone episodes over days at risk.
Figure 12:
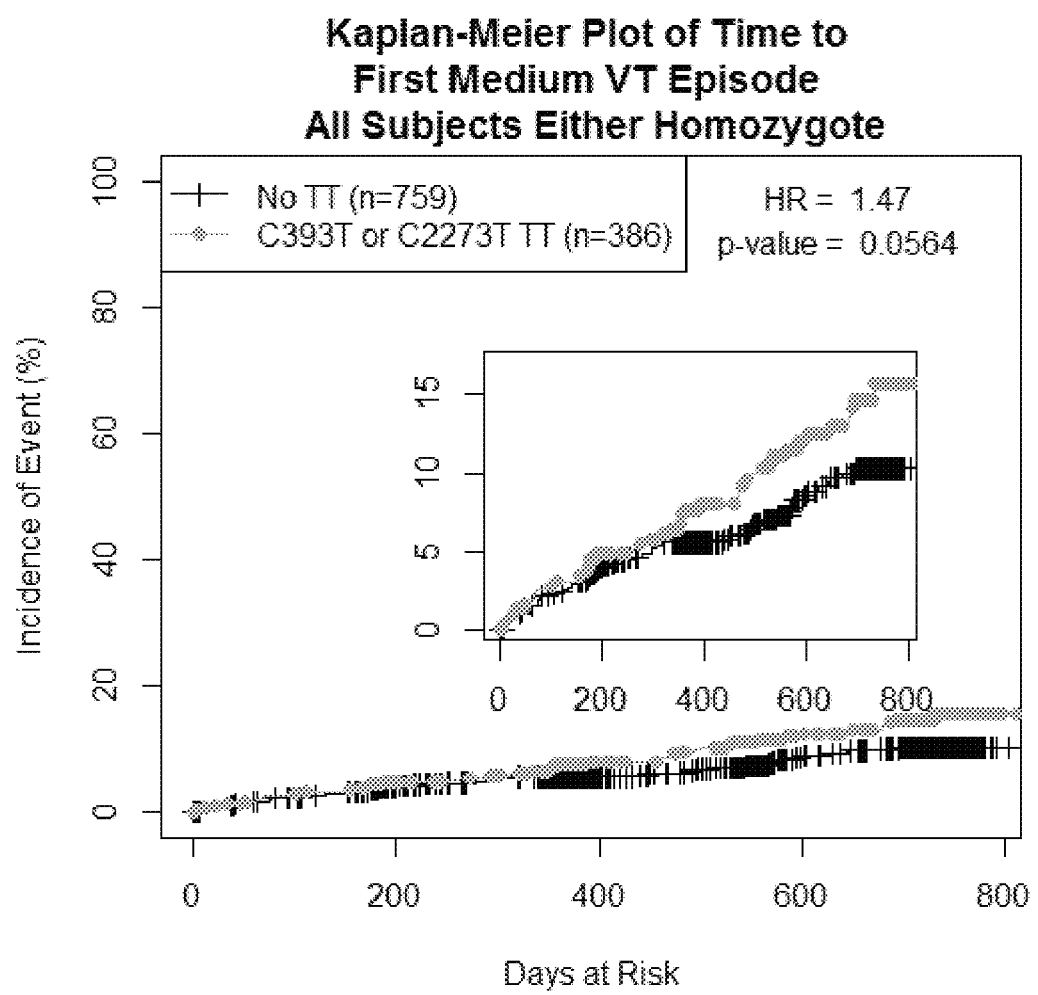
FIG. 12 shows a plot showing the results of the DISCOVERY study for the homozygosity in either GNAS c393 or GNAS c2273 as incidence of Medium VT zone episodes over days at risk.
Figure 13:
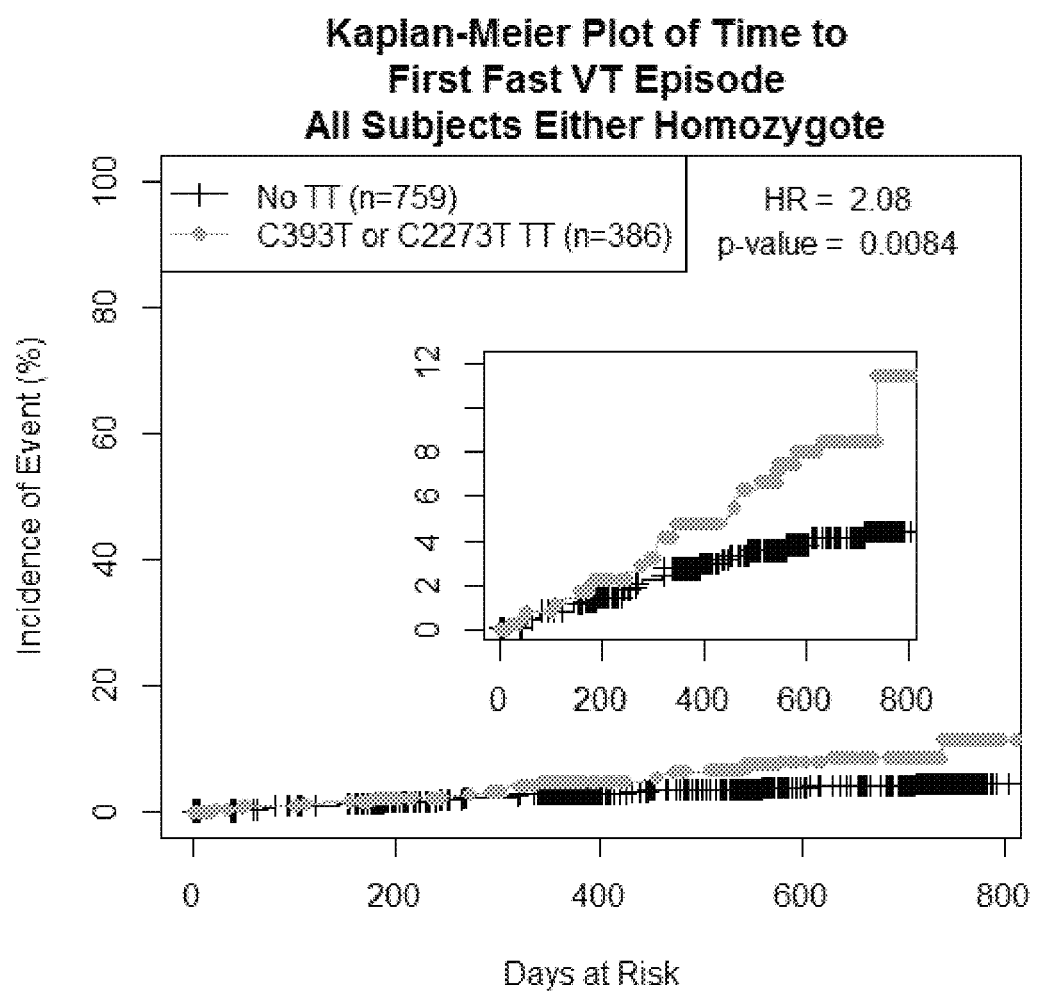
FIG. 13 shows a plot showing the results of the DISCOVERY study for the homozygosity in either GNAS c393 or GNAS c2273 as incidence of Fast VT zone episode over days at risk.

As explained herein, because VT/VF episodes are treated, it is not possible to fully understand whether the episodes would have been lethal without treatment. An alternative to determining whether episodes would have been lethal is to classify them by their cycle length (or the corresponding beats per minute). Separate time to event analyses were done for episodes that fell into each of the three zones. Slow zone was defined as VT cycle length of >300 and ≤400 ms); Medium zone was defined as VT cycle length of >240 and ≤300 ms; and Fast zone was defined as VT cycle length of ≤240 ms. Kaplan Meier plots for each zone are shown in FIG. 11-13. As is shown in FIGS. 11-13, the risk of arrhythmia is increased significantly in all zones in patients with the TT genotype in either region. $T_H$ was a statistically significant predictor of episode incidence in the Slow zone (p=0.0071; HR=1.42) and the Fast zone (p=0.0084; HR=2.08) and was nearly a significant predictor of episode incidence in the Medium zone (p=0.0564; HR=1.47).

Figure 14:
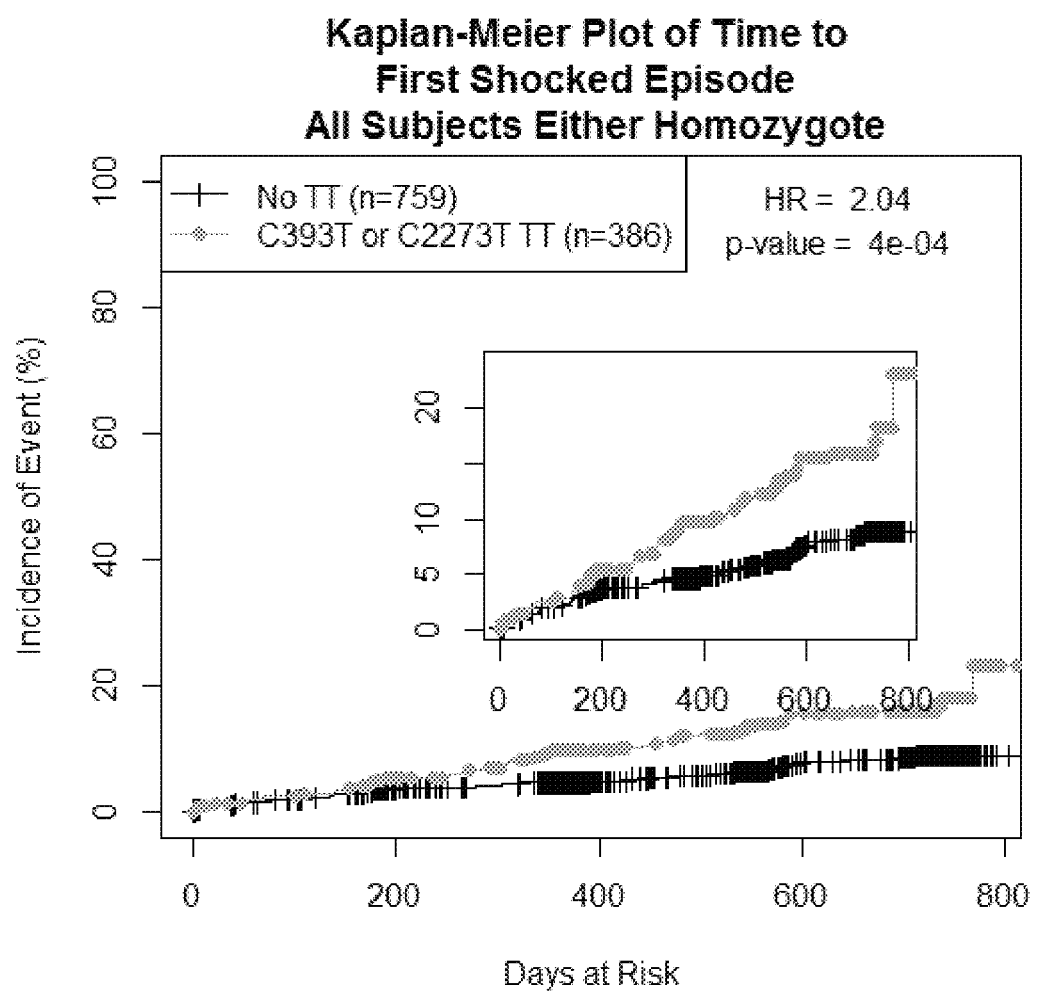
FIG. 14 shows a plot showing the results of the DISCOVERY study for the homozygosity in either GNAS c393 or GNAS c2273 as first shocked episode over days at risk.
Figure 15:
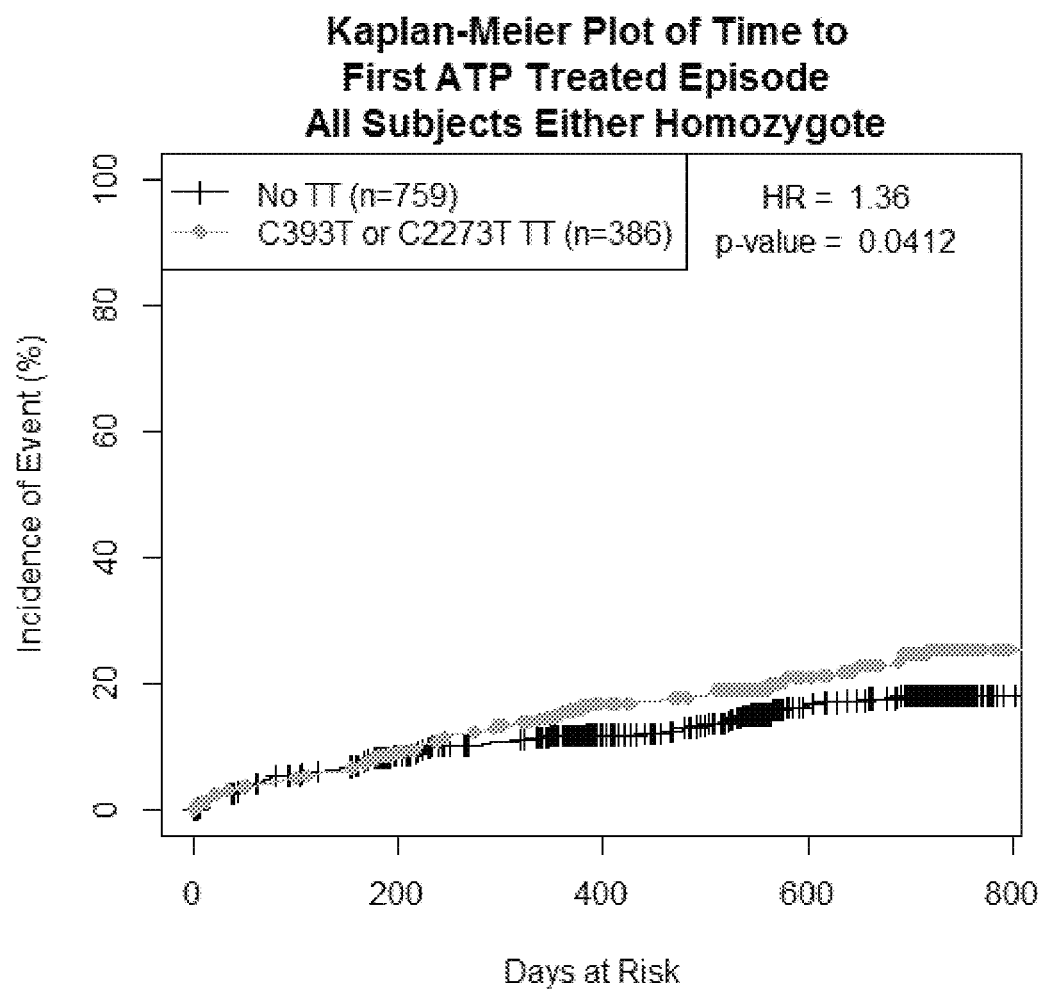
FIG. 15 shows a plot showing the results of the DISCOVERY study for the homozygosity in either GNAS c393 or GNAS c2273 as first ATP treated episode over days at risk.

The time to the first treated episode was also determined. Episodes were classified as shocked, ATP-only or any therapy. Kaplan Meier plots for each treatment are shown in FIGS. 14-16. As is shown in FIGS. 11-16, the presence of the TT genotype in either region is associated with a 58% increased risk of arrhythmia; this effect was independent of arrhythmia cycle length or the treatment studied.

It should be understood that the above-described embodiments and examples are merely illustrative of some of the many specific embodiments that represent the principles of the present invention. Any features disclosed as part of an embodiment of an aspect of the invention can be included in that aspect of the invention alone or in combination. Numerous other versions can be readily devised by those skilled in the art without departing from the scope of the present invention.

We claim:

1. A method, comprising:
   treating a patient identified as having an increased risk of Ventricular tachycardia (VT) and ventricular fibrillation (VF) due to having a history of ischemic cardiomyopathy and a TT genotype in SEQ ID NO. 1;
   wherein the step of treating the patient comprises treating the patient with at least one of a combination CRT pacemaker having defibrillation technology (CRT-D), an Implantable Cardioverter Defibrillator (ICD), and pharmacological therapy.

2. The method of claim 1, further comprising the steps of:
   detecting one or more Single Nucleotide Polymorphisms (SNPs) associated with Sudden Cardiac Arrest (SCA), Sudden Cardiac Death (SCD), Ventricular Arrhythmia (VA) or Heart Failure (HF) in a patient by utilizing at least one probe that overlaps a polymorphic position of SEQ ID NO. 1 where the polymorphic position is flanked on either the 5' and 3' side by a single base pair, to any number of base pairs flanking the 5' and 3' side of the polymorphic position sufficient to identify the SNP or result in a hybridization; and
   assessing the presence of hybridization of the at least one probe to determine if a patient possesses a TT genotype in SEQ ID NO. 1.

3. The method of claim 2, wherein the at least one probe has a length selected from the group of 12 to 101, 25 to 35, 18 to 30, 17 to 24, 15 to 101, 17 to 101, 19 to 101, 21 to 101, 24 to 101, 26 to 101, 15 to 50, 17 to 50, 19 to 50, 21 to 50, 24 to 50, and 26 to 50 nucleotides.

4. The method of claim 2, wherein the at least one probe is capable of being detected by electrical, fluorescent or radioactive means.

5. The method of claim 2, further comprising the step of amplifying a DNA sample prior to utilizing the at least one probe.

6. The method of claim 5, wherein the amplified DNA sample is labeled with a detectable label, and the at least one probe is immobilized to a known location on a solid support; and
   wherein assessing the presence of hybridization of the at least one probe comprises detecting the location of the detectable label with respect to the solid support;
   wherein the detectable label is detectable by at least one of by spectroscopic, photochemical, biochemical, immunochemical, electrical, optical, and chemical means.

7. The method of claim 2, wherein the at least one probe is an Allele Specific Oligomer (ASO).

8. The method of claim 2, wherein the SNP is bi-allelic.

9. The method of claim 2, wherein the at least one probe is selected from the group of sense, anti-sense, and naturally occurring mutants, of SEQ ID NO. 1.

10. The method of claim 2, further comprising the steps of:
    determining a risk for SCA, SCD, VA, or HF based on the presence of hybridization and a history of either ischemic cardiomyopathy or non-ischemic cardiomyopathy for the patient.

11. The method of claim 1, wherein the step of treating the patient comprises implanting a combination CRT pacemaker having defibrillation technology (CRT-D) or an Implantable Cardioverter Defibrillator (ICD).

12. The method of claim 1, wherein the step of treating the patient comprises administering at least one of: a β-blocker and an angiotensin converting enzyme (ACE) inhibitor.

13. The method of claim 2, further comprising the step of determining a hazard ratio for the patient based on the hybridization.

14. The method of claim 2, wherein the step of detecting the SNPs comprises using a diagnostic kit comprising the at least one probe.

15. The method of claim 14, wherein the diagnostic kit comprises a computer processor programmed with software for extracting information of a hybridization of the at least one probe in the diagnostic kit.

\* \* \* \* \*

SEQUENCE LISTING

<160> NUMBER OF SEQ ID NOS: 13

<210> SEQ ID NO 1
<211> LENGTH: 51
<212> TYPE: DNA
<213> ORGANISM: Homo sapiens
<220> FEATURE:
<221> NAME/KEY: y
<222> LOCATION: (26)..(26)
<223> OTHER INFORMATION: y is t/u or c

<400> SEQUENCE: 1
agaaccagtt cagagtggac tacatyctga gtgtgatgaa cgtgcctgac t          51

<210> SEQ ID NO 2
<211> LENGTH: 51
<212> TYPE: DNA
<213> ORGANISM: Homo sapiens
<220> FEATURE:
<221> NAME/KEY: y
<222> LOCATION: (26)..(26)
<223> OTHER INFORMATION: y is t/u or c

<400> SEQUENCE: 2
ttgcctctgg cctaggaatc tgcagyttaa gccagtgaca caatattttg c          51

<210> SEQ ID NO 3
<211> LENGTH: 51
<212> TYPE: DNA
<213> ORGANISM: Homo sapiens
<220> FEATURE:
<221> NAME/KEY: y
<222> LOCATION: (26)..(26)
<223> OTHER INFORMATION: y is t/u or c

<400> SEQUENCE: 3
tctgcagctt aagccagtga cacaayattt tgcattttta aatggtgatt c          51

<210> SEQ ID NO 4
<211> LENGTH: 51
<212> TYPE: DNA
<213> ORGANISM: Homo sapiens
<220> FEATURE:
<221> NAME/KEY: r
<222> LOCATION: (26)..(26)
<223> OTHER INFORMATION: r is g or a

<400> SEQUENCE: 4
gccgccaggc gcacggcgta ggggarcctc gcaggcggcg gcggcggcgg c          51

<210> SEQ ID NO 5
<211> LENGTH: 51
<212> TYPE: DNA
<213> ORGANISM: Homo sapiens

```
<220> FEATURE:
<221> NAME/KEY: r
<222> LOCATION: (26)..(26)
<223> OTHER INFORMATION: r is g or a

<400> SEQUENCE: 5
ctctcgccgc caggcgcacg gcgtarggga gcctcgcagg cggcggcggc g          51

<210> SEQ ID NO 6
<211> LENGTH: 52
<212> TYPE: DNA
<213> ORGANISM: Homo sapiens
<220> FEATURE:
<221> NAME/KEY: ky
<222> LOCATION: (26)..(26)
<223> OTHER INFORMATION: k is g or t/u and y is c or t/u

<400> SEQUENCE: 6
ctgagtgtga tgaacgtgcc tgactkycca gcccgggagc cgcgcgggcg ag         52

<210> SEQ ID NO 7
<211> LENGTH: 51
<212> TYPE: DNA
<213> ORGANISM: Homo sapiens
<220> FEATURE:
<221> NAME/KEY: y
<222> LOCATION: (26)..(26)
<223> OTHER INFORMATION: y is t/u or c

<400> SEQUENCE: 7
agagcatcat ctgcggcatc acgtcygtgg ccttctccct cagtggccgc c          51

<210> SEQ ID NO 8
<211> LENGTH: 51
<212> TYPE: DNA
<213> ORGANISM: Homo sapiens
<220> FEATURE:
<221> NAME/KEY: r
<222> LOCATION: (26)..(26)
<223> OTHER INFORMATION: r is g or a

<400> SEQUENCE: 8
tggtcttctc ggtgcgcagc ccctcrtggg tgctcaactt cctgctgcag a          51

<210> SEQ ID NO 9
<211> LENGTH: 51
<212> TYPE: DNA
<213> ORGANISM: Homo sapiens
<220> FEATURE:
<221> NAME/KEY: y
<222> LOCATION: (26)..(26)
<223> OTHER INFORMATION: y is t/u or c

<400> SEQUENCE: 9
tttttttttt tttttttttt gtcctyctca aggtgggagg ggggattgag a          51

<210> SEQ ID NO 10
<211> LENGTH: 51
<212> TYPE: DNA
<213> ORGANISM: Homo sapiens
<220> FEATURE:
<221> NAME/KEY: m
<222> LOCATION: (26)..(26)
<223> OTHER INFORMATION: m is a or c

<400> SEQUENCE: 10
ccttgataat ttggctatct gaatamattt gtgaatttgc taggttaaga c          51
```

```
<210> SEQ ID NO 11
<211> LENGTH: 51
<212> TYPE: DNA
<213> ORGANISM: Homo sapiens
<220> FEATURE:
<221> NAME/KEY: r
<222> LOCATION: (26)..(26)
<223> OTHER INFORMATION: r is g or a

<400> SEQUENCE: 11
agtatgcgta taacttgatt tcaaartata aatctggaaa agtctagaat c          51

<210> SEQ ID NO 12
<211> LENGTH: 51
<212> TYPE: DNA
<213> ORGANISM: Homo sapiens
<220> FEATURE:
<221> NAME/KEY: s
<222> LOCATION: (26)..(26)
<223> OTHER INFORMATION: s is g or c

<400> SEQUENCE: 12
tcagtttcca catttatgaa atgtgsctga aaaattattt taagatcatt g          51

<210> SEQ ID NO 13
<211> LENGTH: 59
<212> TYPE: DNA
<213> ORGANISM: Homo sapiens
<220> FEATURE:
<221> NAME/KEY: misc_feature
<222> LOCATION: (26)..(34)
<223> OTHER INFORMATION: can be absent or ttttttt

<400> SEQUENCE: 13
cgtggtttct ttttttttttt tttttttttt ttttgtcctc ctcaaggtgg gaggggga   59
```